(12) United States Patent
Cragg et al.

(10) Patent No.: US 6,544,236 B1
(45) Date of Patent: Apr. 8, 2003

(54) DEVICE, SYSTEM AND METHOD FOR IMPROVING DELIVERY OF HEMOSTATIC MATERIAL

(75) Inventors: Andrew H. Cragg, Edina, MN (US); Rodney Brenneman, San Juan Capistrano, CA (US); Mark Ashby, Laguna Niguel, CA (US)

(73) Assignee: Sub-Q, Incorporated, San Clemente, CA (US)

( * ) Notice: Subject to any disclaimer, the term of this patent is extended or adjusted under 35 U.S.C. 154(b) by 5 days.

(21) Appl. No.: 09/687,590

(22) Filed: Oct. 13, 2000

Related U.S. Application Data

(63) Continuation of application No. 09/334,700, filed on Jun. 16, 1999, now Pat. No. 6,200,328, which is a continuation-in-part of application No. 09/247,880, filed on Feb. 10, 1999, now Pat. No. 6,086,607.
(60) Provisional application No. 60/159,406, filed on Oct. 14, 1999.

(51) Int. Cl.[7] ................................................. A61M 5/00
(52) U.S. Cl. .................... 604/254; 604/256; 604/272
(58) Field of Search ........................... 606/213; 604/15, 604/240–243, 51, 411, 272, 285, 254, 256

(56) References Cited

U.S. PATENT DOCUMENTS

| 581,235 A | 4/1897 | Kenyon |
| 1,578,517 A | 3/1926 | Hein |
| 2,086,580 A | 7/1937 | Shirley |
| 2,465,357 A | 3/1949 | Correll |
| 2,492,458 A | 12/1949 | Bering, Jr. |
| 2,507,244 A | 5/1950 | Correll |

(List continued on next page.)

FOREIGN PATENT DOCUMENTS

| EP | 032826 A2 | 7/1981 |
| EP | 476178 A1 | 3/1992 |
| EP | 482350 A2 | 4/1992 |
| FR | 2 641 692 | 7/1990 |
| GB | 1509023 | 4/1978 |
| GB | 1569660 | 6/1980 |
| RU | 782814 | 11/1980 |
| RU | 1088709 A | 4/1984 |
| WO | WO 96/08208 | 3/1996 |
| WO | WO 98/06346 | 2/1998 |

OTHER PUBLICATIONS

Vincent P. Chuang, M.D., et al., "Sheath Needle for Liver Biopsy in High–Risk Patients", *Radiology*, 166:261–262 (1988).
David J. Allison, M.D., et al., "Percutaneous Liver Biopsy and Track Embolization with Steel Coils", *Radiology*, 169(1):261–263 (1988).
Sigmund Silber, M.D., FACC, "Rapid Hemostasis of Arterial Puncture Sites with Collagen in Patients Undergoing Diagnostic and Interventional Cardiac Catheterization", *Clinical Cardiology*, 20:981–992 (1997).

(List continued on next page.)

*Primary Examiner*—Gary Jackson
(74) *Attorney, Agent, or Firm*—Thelen Reid & Priest LLP; Robert E. Krebs

(57) ABSTRACT

A device, system and method for improving delivery of hemostatic material, in which the device includes a vent cap body capable of removably engaging a cannula. The vent cap has a passage extending through the vent cap body from the cannula to an exterior of the vent cap body where a restricter for restricting the flow of fluid from the cannula to the exterior. In one embodiment, the vent cap has a valve which has an opened and closed position. In the closed position, the valve is designed to provide a back pressure or resistence. When a certain force is applied against the valve, the valve moves from the closed position to the opened position, where a gas or fluid may pass through the vent cap. The vent cap is designed to help maintain the continuity of the hemostatic material during delivery of the material from the adaptor to the trial staging chamber.

44 Claims, 17 Drawing Sheets

U.S. PATENT DOCUMENTS

| | | |
|---|---|---|
| 2,558,395 A | 6/1951 | Studer |
| 2,597,011 A | 5/1952 | MacMasters et al. |
| 2,680,442 A | 6/1954 | Linzmayer |
| 2,761,446 A | 9/1956 | Reed |
| 2,814,294 A | 11/1957 | Figge |
| 2,824,092 A | 2/1958 | Thompson |
| 2,899,362 A | 8/1959 | Sieger, Jr. et al. |
| 3,157,524 A | 11/1964 | Artandi |
| 3,724,465 A | 4/1973 | Duchane |
| 4,000,741 A | 1/1977 | Binard et al. |
| 4,323,072 A | 4/1982 | Rosenbluth et al. |
| 4,340,066 A | 7/1982 | Shah |
| 4,390,018 A | 6/1983 | Zukowski |
| 4,515,637 A | 5/1985 | Cioca |
| 4,587,969 A | 5/1986 | Gillis |
| 4,588,395 A | 5/1986 | Lemelson |
| 4,619,261 A | 10/1986 | Guerrero |
| 4,619,913 A | 10/1986 | Luck et al. |
| 4,645,488 A | 2/1987 | Matukas |
| 4,744,364 A | 5/1988 | Kensey |
| 4,790,819 A | 12/1988 | Li et al. |
| 4,829,994 A | 5/1989 | Kurth |
| 4,850,960 A | 7/1989 | Grayzel |
| 4,852,568 A | 8/1989 | Kensey |
| 4,890,612 A | 1/1990 | Kensey |
| 4,900,303 A | 2/1990 | Lemelson |
| 4,929,246 A | 5/1990 | Sinofsky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,053,046 A | 10/1991 | Janese |
| 5,061,274 A | 10/1991 | Kensey |
| 5,080,655 A | 1/1992 | Haaga |
| 5,108,421 A | 4/1992 | Fowler |
| 5,163,904 A | 11/1992 | Lampropoulos et al. |
| 5,167,624 A | 12/1992 | Butler et al. |
| 5,192,300 A | 3/1993 | Fowler |
| 5,192,301 A | 3/1993 | Kamiya et al. |
| 5,195,988 A | 3/1993 | Haaga |
| 5,220,926 A | 6/1993 | Jones |
| 5,221,259 A | 6/1993 | Weldon et al. |
| 5,275,616 A | 1/1994 | Fowler |
| 5,310,407 A | 5/1994 | Casale |
| 5,325,857 A | 7/1994 | Nabai et al. |
| 5,334,216 A | 8/1994 | Vidal et al. |
| 5,366,480 A | 11/1994 | Corriveau et al. |
| 5,383,896 A | 1/1995 | Gershony et al. |
| 5,383,899 A | 1/1995 | Hammerslag |
| 5,388,588 A | 2/1995 | Nabai et al. |
| 5,391,183 A | 2/1995 | Janzen et al. |
| 5,419,765 A | 5/1995 | Weldon et al. |
| 5,431,639 A | 7/1995 | Shaw |
| 5,437,631 A | 8/1995 | Janzen |
| 5,467,780 A | 11/1995 | Nabai et al. |
| 5,478,352 A | 12/1995 | Fowler |
| 5,479,936 A | 1/1996 | Nabai et al. |
| 5,486,195 A | 1/1996 | Myers et al. |
| 5,522,850 A | 6/1996 | Yomtov et al. |
| 5,526,822 A | 6/1996 | Burbank et al. |
| 5,529,577 A | 6/1996 | Hammerslag |
| 5,540,715 A | 7/1996 | Katsaros et al. |
| 5,542,914 A | 8/1996 | Van Iten |
| 5,545,178 A | 8/1996 | Kensey et al. |
| 5,558,853 A | 9/1996 | Quay |
| 5,591,204 A | 1/1997 | Janzen et al. |
| 5,591,205 A | 1/1997 | Fowler |
| 5,601,602 A | 2/1997 | Fowler |
| 5,645,566 A | 7/1997 | Brenneman et al. |
| 5,649,547 A | 7/1997 | Ritchart et al. |
| 5,653,730 A | 8/1997 | Hammerslag |
| 5,665,107 A | 9/1997 | Hammerslag |
| 5,676,689 A | 10/1997 | Kensey et al. |
| 5,681,279 A | 10/1997 | Roper et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,775,333 A | 7/1998 | Burbank et al. |
| 5,810,806 A | 9/1998 | Ritchart et al. |
| 5,830,130 A | 11/1998 | Janzen et al. |
| 5,902,310 A | 5/1999 | Foerster et al. |
| 5,997,486 A | * 12/1999 | Burek et al. ............... 600/573 |
| 6,007,563 A | 12/1999 | Nash et al. |
| 6,071,301 A | 6/2000 | Cragg et al. |
| 6,162,192 A | 12/2000 | Cragg et al. |

OTHER PUBLICATIONS

Ferdinand Kiemeneij, MD, et al., "Improved Anticoagulation Management After Palmaz Schatz Coronary Stent Implantation by Sealing the Arterial Puncture Site With a Vascular Hemostasis Device", *Catheterization and Cardiovascular Diagnosis*, 30:317–322 (1993).

J.P.M. Foran, et al., "*Early Mobilisation After Percutaneous Cardiac Catheterisation Using Collagen Plug (VasoSeal) Haemostasis*," Br Heart, vol. 69 (1993) pp. 424–429.

Schrader, R., "*Collagen Application*," Catheterization and Cardiovascular Diagnosis, (1992) pp. 298–302.

JSR Gibbs, "*Fermoral Arterial Hemostasis*," Journal of Interventional Cardiology, v 5 (1992) pp 85–88.

W.G. Kussmaul, "*Rapid Arterial Hemostasis*," Journal of the American College of Cardiology, vol. 25 (1995) pp. 1685–1692.

Timothy A. Sanborn, MD, et al., "*Multicenter Randomized Trial Comparing a Percutaneous Collagen Hemostasis Device With Conventional Manual Compression After Diagnostic Angiography and Angioplasty*," Journal of American College of Cardiology, vol. 22, No. 5 (1993) pp. 1273–1279.

Pharmacia & Upjohn Manufacturer Brochure "*Gelfoam Sterile Sponge, Sterile Powder, and Sterile Film*," (May 1997): pp. 1–34.

Pharmacia & Upjohn Manufacturer Brochure, "*Gelfoam Sterile Powder*,"(Feb. 1996).

Pharmacia & Upjohn Manufacturer Brochure "*Gelfoam Sterile Powder,* " (Mar. 1996).

Pharmacia & Upjohn Manufacturer Specification "*Gelfoam Sterile Sponge, Sterile Powder, and Sterile Film*," (Nov. 1996): pp. 1–23.

Pharmacia & Upjohn Manufacturer Brochure for Gelfoam, 1996.

* cited by examiner

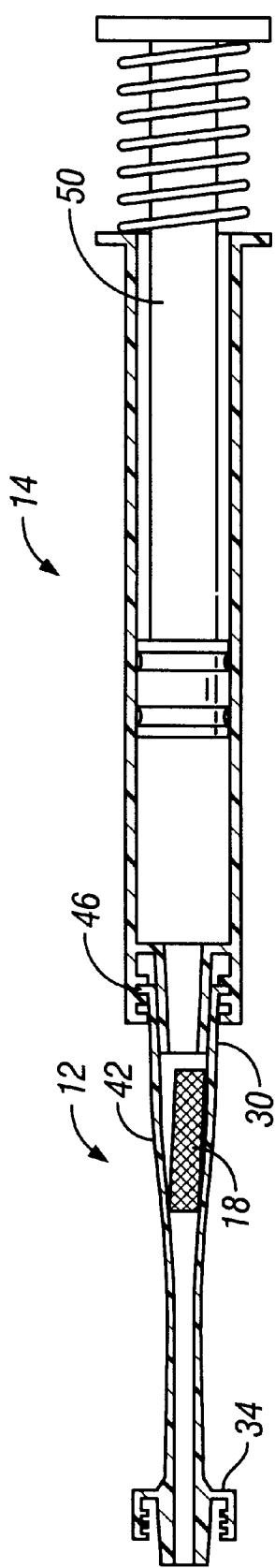
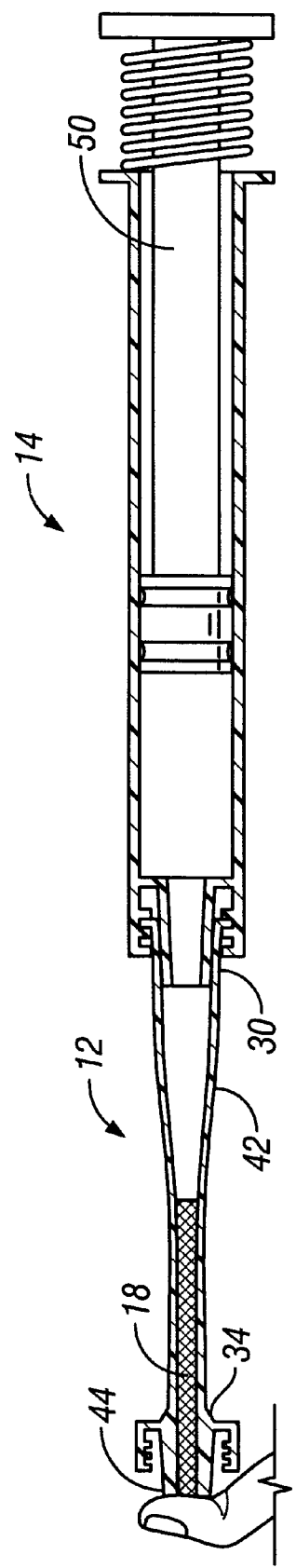
FIG. 4
FIG. 5

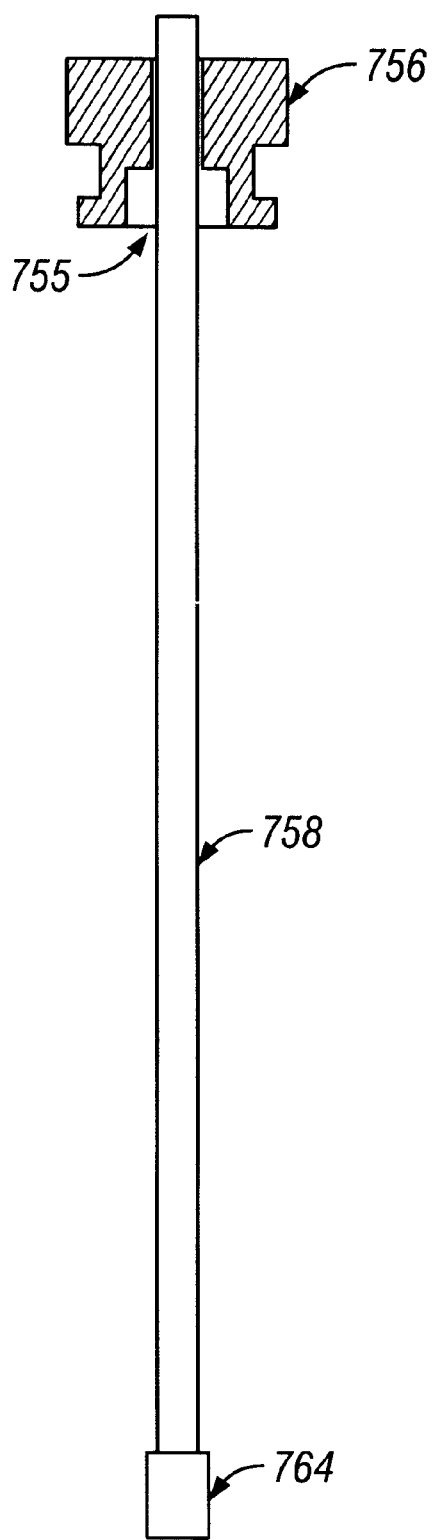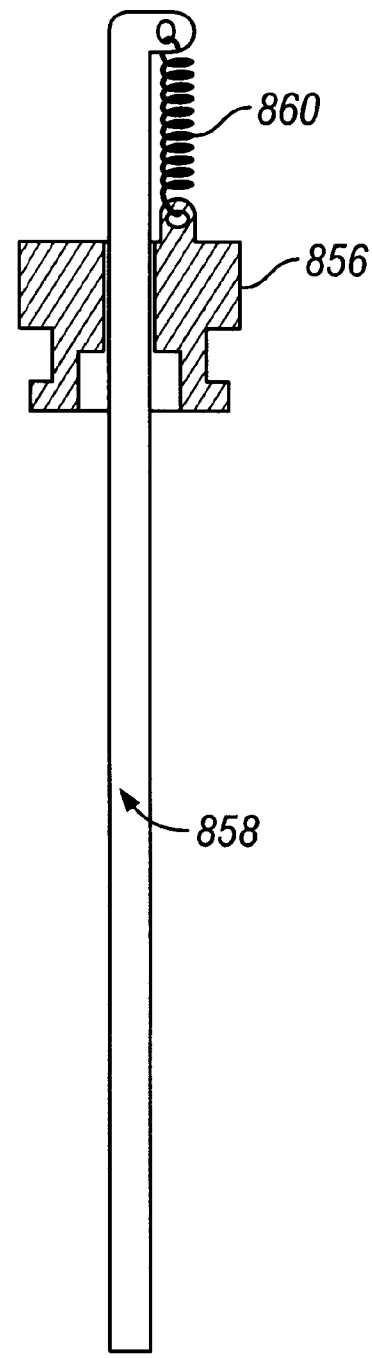
FIG. 26
FIG. 27

DEVICE, SYSTEM AND METHOD FOR IMPROVING DELIVERY OF HEMOSTATIC MATERIAL

CROSS-REFERENCE TO RELATED APPLICATION

This application claims priority to provisional U.S. Application Ser. No. 60/159,406 filed Oct. 14, 1999. This application is also a continuation of U.S. Application Ser. No. 09/334,700 filed Jun. 16, 1999, now U.S. Pat. No. 6,200,328 entitled "DEVICE, SYSTEM AND METHOD FOR IMPROVING DELIVERY OF HEMOSTATIC MATERIAL" which is a continuation-in-part of U.S. application Ser. No. 09/247,880 filed Feb. 10, 1999, now U.S. Pat. No. 6,086,607 which is a continuation-in-part of U.S. application Ser. No. 09/071,670 filed May 1, 1998, now U.S. Pat. No. 6,071,301 which all have the same inventors Andrew H. Cragg, Rodney Brenneman, and Mark Ashby and are all hereby incorporated by reference in their entirely.

BACKGROUND OF THE INVENTION

1. Field of the Invention

The invention relates to a device, system and method for improving delivery of hemostatic material by the use of a vent cap.

2. Brief Description of the Related Art

A percutaneous needle biopsy of solid organs is one of the most common interventional medical procedures. Millions of percutaneous needle biopsies are performed annually in the United States and throughout the world. A percutaneous biopsy is a safe procedure which has supplanted a surgical biopsy for many indications, such as skin biopsy and liver biopsy.

Possible complications of a needle biopsy include bleeding at the biopsy site. The amount of bleeding is related to a number of factors including needle size, tissue sample size, patient's coagulation status, and the location of the biopsy site. Vascular organs such as the liver, a common biopsy target, may bleed significantly after a needle biopsy. To minimize bleeding from a biopsy site, small gauge needles are typically used. Small gauge needles, however, produce less satisfactory biopsy specimens but frequently are favored over larger bored needles because of their perceived safety. In order to minimize the chance of internal bleeding after a biopsy, external pressure is applied and patients are often asked to lie in uncomfortable positions, such as the lateral decubitus position, for a number of hours, particularly after a liver biopsy.

Sterile sponges, such as Gelfoam, are prepared in dry sterile sheets which are used as packing material during surgery for control of bleeding. The sponge sheets are left in the surgical site after surgery to stop bleeding and are absorbed by the body in one to six weeks. A number of techniques have used these absorbable sterile sponge materials to plug a biopsy tract to minimize or prevent bleeding. The absorbable sponge provides a mechanical blockage of the tract, encourages clotting, and minimizes bleeding though the biopsy tract. Despite the advantages of using an absorbable sponge to plug a biopsy tract this technique has not achieved widespread use because of difficulty in preparing and delivering the sponge material into the biopsy tract.

One example of a biopsy wound closure device using an implantable sponge is described in U.S. Pat. No. 5,388,588. According to this patent, a circular sponge of an absorbable foam material is precut and inserted into a biopsy site by an applicator rod having the sponge positioned on the end. Once the sponge is implanted, the sponge absorbs blood and swells to fill the tract preventing further bleeding at the biopsy site. However, the sponge is difficult to deliver and expands slowly once delivered. In addition, this delivery method can only deliver a sponge of a limited size which provides less local compression than desired and may incompletely fill the target site. Further, bleeding may continue along sections of the biopsy tract where no sponge has been delivered.

Accordingly, it would be desirable to provide a device, system and method for improving the delivery of hemostatic material by the use of a vent cap which restricts the flow of fluid through the vent cap.

SUMMARY OF THE INVENTION

The present invention relates to a device, system and method for improving delivery of hemostatic material by use of a vent cap.

In accordance with one aspect of the present invention, a device for improving delivery of hemostatic material includes a vent cap body capable of removably engaging a cannula, a passage extending through the vent cap body from the cannula to an exterior of the vent cap body, and a restricter for restricting a fluid from flowing from the cannula to the exterior through the passage.

In accordance with another aspect of the present invention, a system for improving delivery of hemostatic material includes an elongated cannula having a first end, a second end, and a lumen extending from the first end to the second end, and a vent cap body capable of removably engaging the second end, the vent cap body having a passage extending through the vent cap body from the cannula to an exterior of the vent cap body and a restricter for restricting a fluid from flowing from the fitting to the exterior through the passage.

In accordance with another aspect of the present invention, a method of preparing and delivering hemostatic material to a patient includes inserting a pledget of sponge material into a cannula, connecting a vent cap to the cannula, restricting a flow of fluid through the cannula and vent cap by use of a restricter, hydrating the sponge, and delivering the hydrated sponge to the patient.

For a better understanding of the present invention, together with other and further objects thereof, reference is made to the following description, taken in conjunction with accompanying drawings, and its scope will be pointed out in the appending claims.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 4 is a side cross sectional view of an adaptor and syringe combination with a pledget positioned within the adaptor;

FIG. 5 is a side cross sectional view of an adaptor and syringe combination in which the pledget has been hydrated and moved into a small diameter end of the adaptor;

FIG. 26 is a side cross sectional view of an alternative embodiment of a vent cap with the rod extending through the vent cap; and FIG. 27 is a partial side cross sectional view of an alternative embodiment of a vent cap with a rod extending through the vent cap.

DETAILED DESCRIPTION OF THE PREFERRED EMBODIMENTS

The device, system and method according to the present invention are used in connection with a delivery system for delivery of a bio-compatible sponge in a hydrated condition to achieve hemostatis. The apparatus for delivering a hydrated sponge will be described below in connection with treatment of a biopsy tract after a percutaneous needle biopsy. However, the invention may be used for facilitating hemostasis of other types of puncture wounds or tissue access tracts to prevent bleeding of these wounds.

Figure 1:
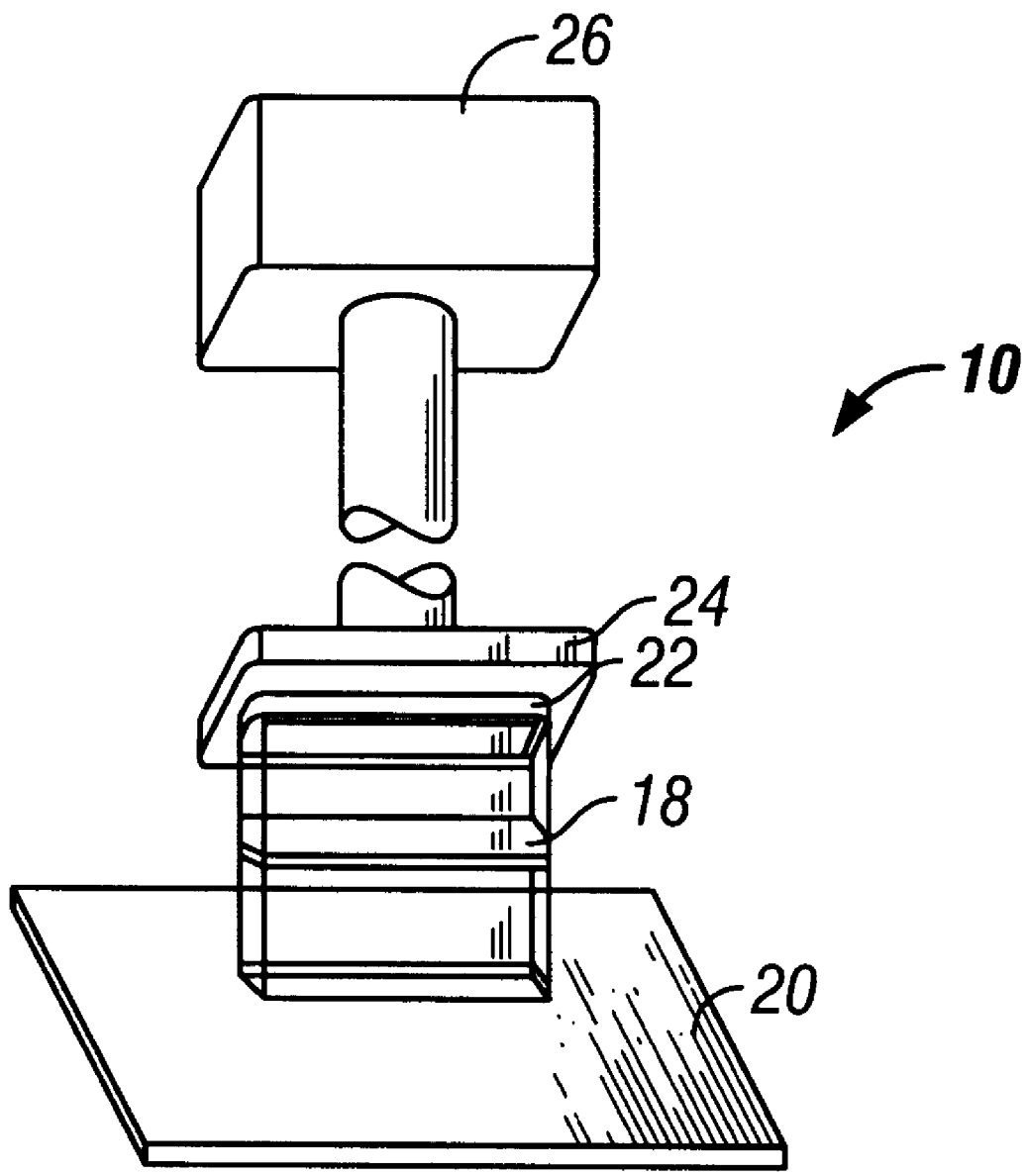
FIG. 1 is a perspective view of a punch for forming pledgets.
Figure 2:
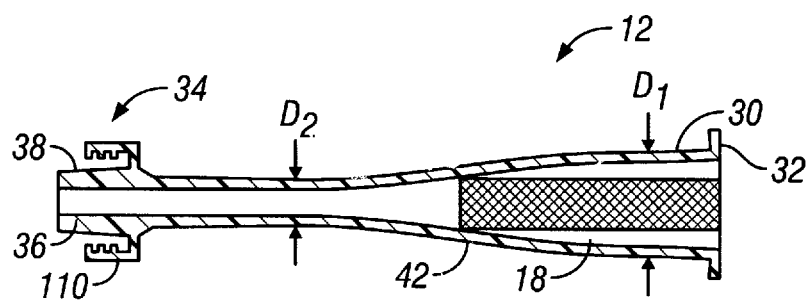
FIG. 2 is a side cross sectional view of an adaptor for delivery of a pledget to a needle.
Figure 3:
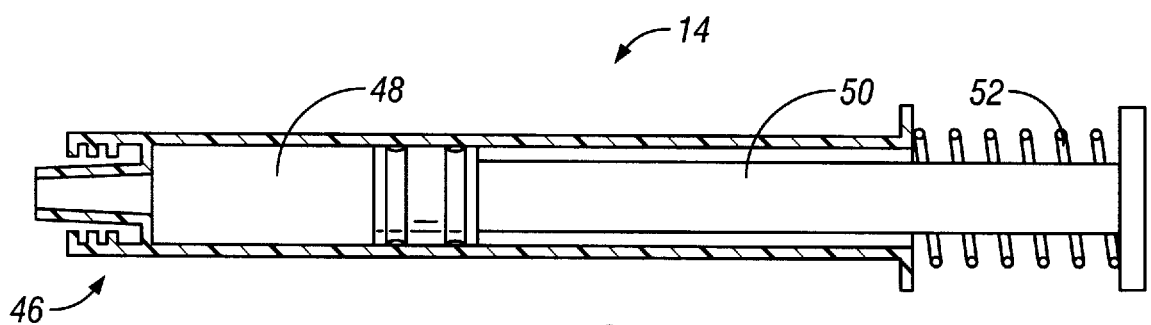
FIG. 3 is a side cross sectional view of a syringe for connection to the adaptor.

The system for facilitating hemostasis of the biopsy tract, as shown in FIGS. 1–3, includes a punch 10 for cutting a pledget 18 of sponge material from a sheet of this material, an adaptor 12 for delivering the pledget to a biopsy needle 16, and a syringe 14 for hydrating and injecting the pledget. The adaptor 12 allows a relatively large pledget of sponge material to be compressed and inserted into the biopsy tract in a hydrated state. The sponge material for use in facilitating hemostasis may be any sponge which is capable of deforming upon hydration to be delivered by fluid pressure through a biopsy needle or other cannula.

Prior to discussing the present invention in further detail, the following terms are defined:

"Pledget" means a piece of absorbable sponge of a generally elongated shape having a size which allows injection in a hydrated state through a biopsy needle or other cannula.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which when implanted within a human or other mammalian body is absorbed by the body.

"Hydrate" means to partially or fully saturate with a fluid, such as, saline, water, contrast agent, thrombin, therapeutic agent, or the like.

"Kneading" of the absorbable sponge material means both dry and wet manipulation of sponge material which compresses, enlarges, or changes the shape of the sponge material causing the sponge material to have improved expansion response.

FIG. 1 illustrates one example of a punch 10, also called a dye cutter, for cutting an absorbable sponge sheet 20 into pledgets 18 of an appropriate size for delivery to a biopsy tract. The punch 10 includes a rectangular blade 22 fixed to a plate 24 having a handle 26. The punch 10 is pressed down onto a flat sheet 20 of commercially available absorbable sponge to cut the pledget 18 of an appropriate size. In addition to the punch 10 illustrated in FIG. 1 other cutting devices, such as, a scissor type hand punch, an automatic punching machine, or a templet and knife may be used for preparation of the pledget 18. An alternative pledget forming system will be discussed in further detail below with respect to FIGS. 11–13.

FIG. 2 shows the adaptor 12 in which the pledget 18 is placed for hydration and for delivery through the biopsy needle 16. The adaptor 12 allows pieces of absorbable sponge material with relatively large cross sections to be easily delivered through a biopsy needle 16 with a much smaller cross section. The adaptor 12 also functions to remove air from the pledget 18.

The adaptor 12 which delivers the hydrated pledget 18 to the needle 16 includes a first end 30 having an annular lip 32 or female luer fitting for connection to the syringe 14. A second end 34 of the adaptor 12 has a male luer fitting 36 for connection to a biopsy needle 16 or other cannula. The luer fitting 36 includes a tapered external surface 38 and a retaining ring 40 with internal threads for receiving an annular lip of the biopsy needle. The adaptor 12 has an internal lumen with a first diameter $D_1$ at the first end 30 and a second diameter $D_2$ at the second end 34. Between the first and second ends of the adaptor 12, a tapered section 42 of the adaptor provides a funnel for compressing the hydrated pledget 18 prior to injection through the biopsy needle 16 and needle hub 28.

The adaptor 12 may be formed in any known manner such as by molding from a plastic material. Preferably, the adaptor 12 is transparent so that the pledget 18 can be viewed through the adaptor and the user can visually monitor when the pledget is loaded within the adaptor and when the pledget has been delivered into the needle. The adaptor lumen may be provided with a friction reducing coating for improved delivery. The delivery fluid also reduces friction for improved delivery by wetting the exterior surface of the pledget 18.

Figure 7:
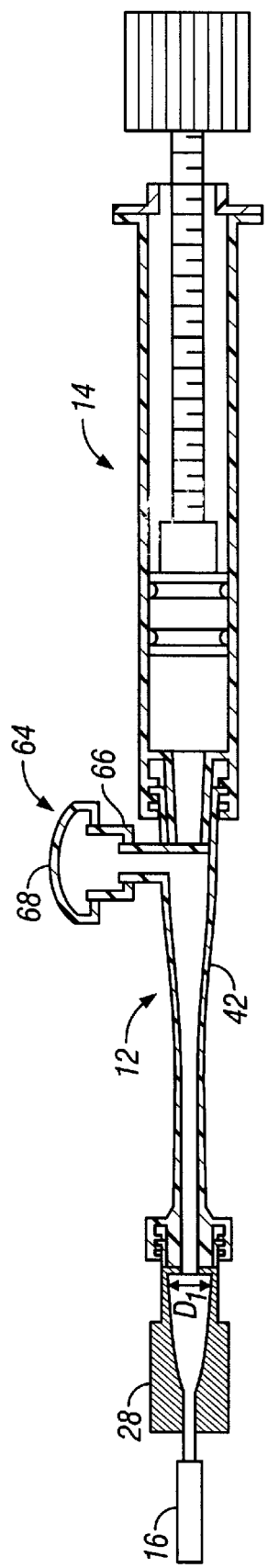
FIG. 7 is a side cross sectional view of an alternative embodiment of an adaptor connected to a biopsy needle and syringe.

The syringe 14, as illustrated in FIGS. 3–5, includes a male luer fitting 46, a fluid chamber 48, and a plunger 50. The first end 30 of the adaptor 12 is connectable to the luer fitting 46 of the conventional syringe 14. The syringe 14 may be provided with a spring 52 for automatic filling of the syringe 14 with a predetermined volume of fluid. Alternatively, the syringe may include a threaded syringe plunger, as shown in FIG. 7, for accurate injection of small quantities of fluid. The syringe volume will vary depending on the amount of fluid needed for hydration and delivery of the pledget 18 through the biopsy needle 16.

Figure 6:
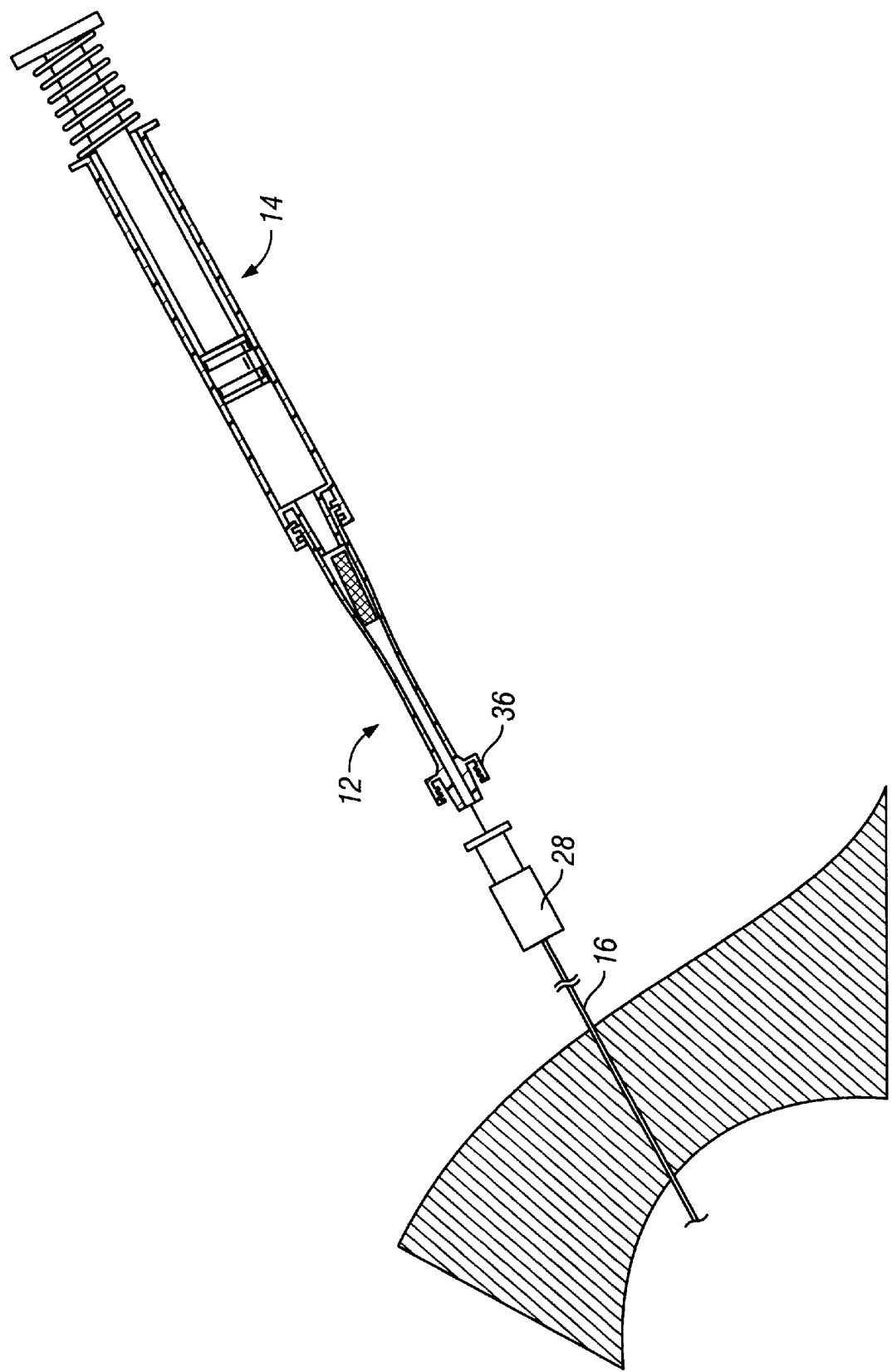
FIG. 6 is a side cross sectional view of the loaded adaptor and syringe combination in preparation for connection to a biopsy needle.

A biopsy needle 16 for use with the present invention is preferably a co-axial biopsy needle, such as a bi-axial or a tri-axial biopsy needle. A co-axial biopsy needle includes an outer needle or cannula through which a tissue sample is removed with a tissue scoop or other biopsy instrument. Once the tissue sample has been removed, the outer cannula remains in the patient as illustrated in FIG. 6. Although the cannula for delivery of the sponge pledget has been described as a biopsy needle, the cannula may be a catheter, sheath, or any other type of cannula.

A preferred method of facilitating hemostasis of a biopsy tract will be described with reference to FIG. 4 which shows the loading and hydration of the pledget 18 within the adaptor 12. A pledget 18 is cut as described above and placed within the adaptor 12 from the first end 30 of the adaptor. The syringe 14 is filled with a predetermined amount of fluid, such as saline, and is connected to the first end 30 of the adaptor 12 by the luer fitting 46. The plunger 50 of the syringe 14 is then depressed, slowly causing fluid to pass into the adaptor 12, hydrating the pledget 18, and filling the adaptor with a column of fluid. Care should be taken to inject the fluid slowly to prevent the pledget from being ejected out of the second end 34 of the adaptor. Preferably, the user waits a few seconds once the fluid is injected into the adaptor 12 until the pledget 18 is adequately hydrated creating a lubricous surface on the pledget. The pledget 18 may expand within the adaptor to fill or nearly fill the lumen of the adaptor. The adaptor 12 with the pledget 18 hydrated within the proximal end is ready to inject the pledget into a biopsy tract to facilitate hemostasis within the biopsy tract. The adaptor 12 may be loaded prior to beginning the biopsy procedure.

After the biopsy procedure has been completed, the outer sheath of the biopsy needle 16 through which the biopsy has been taken is maintained in place within the biopsy tract, as shown in FIG. 6. The biopsy needle 16 provides preestablished targeting of the delivery site for delivery of the absorbable sponge pledget 18 and eliminates the uncertainty of re-access. The luer fitting 36 of the adaptor 12 is connected to the biopsy needle hub 28, as illustrated in FIG. 6. The biopsy needle 16 is withdrawn a short distance, such as about 1 to 20 mm, along the biopsy tract to provide space for the pledget 18 to be received in the biopsy tract. Additional fluid is then rapidly injected by the syringe to move the pledget 18 into the biopsy needle 16. When the adaptor lumen has been blocked by the hydrated pledget 18 which has swelled within the adaptor, injection of additional fluid will push the pledget through the tapered section 42 of the adaptor. If the adaptor lumen has not been entirely blocked by the pledget 18, the venturi effect will help draw the pledget through the tapered section 42 of the adaptor. After the pledget 18 is moved to the biopsy needle 16, the pledget 18 is then delivered from the needle 16 to the biopsy tract by rapid injection of additional fluid by the syringe 14. The hydrated pledget 18 quickly expands upon delivery to fill the available space in the biopsy tract to facilitate hemostasis and provide localized compression.

As illustrated in the cross sectional view of FIG. 7, one example of a needle hub 28 has an interior diameter $D_3$ which is larger than the diameter $D_2$ at the distal end 36 of the adaptor 12. The large internal diameter needle hub 28 allows the hydrated pledget 18 which has been compressed by the tapered section 42 of the adaptor to expand in the needle hub before being compressed again into the needle lumen. This compression and enlargement of the hydrated absorbable sponge material, does not adversely affect the pledget delivery and in fact improves the expansion response of some delivered sponge materials as will be discussed in further detail below.

A smooth tapered transition between the lumen of the needle hub 28 and the needle lumen helps to provide for easy injection of the pledget 18. However, needles having internal steps between the needle hub 28 and the needle 16 have been used and the pledget 18 is still injected successfully. According to an alternative embodiment, the needle hub 28 may be designed to have an inner diameter, which is approximately the same as the inner diameter $D_2$ at the distal end 36 of the adaptor.

Preferably, specific measured doses of fluid are used to achieve each of the steps of the treatment procedure depending on the pledget size and the dimensions of the adaptor 12, the needle 16, and the needle hub 28. The pledget 18 should be completely delivered into the biopsy tract by the fluid and only a minimal amount of extraneous fluid should be delivered. For example, the pledget 18, once inside the needle, may be delivered with about 0.02 to 1.5 ml of fluid depending on the size of the needle 16 used. Injection of larger amounts of fluid may distend the biopsy tract or displace the pledget within the organ.

According to one example, a pledget 18 having a size of approximately 20 mm by 2 mm cut from a sheet of commercially available Gelfoam having a thickness of approximately 1.5 mm can be hydrated and injected through a standard 18 gauge, approximately 15 cm long biopsy needle with approximately 0.9 ml of fluid. An adaptor according to this example has a first diameter D, of about 0.38 cm, a second diameter $D_2$ of about 0.14 cm, a total length of about 3.80 cm, and a taper angle of about 45°. About 0.3 ml of fluid is injected slowly to hydrate the pledget 18 and fill the adaptor with a column of fluid. Approximately 0.3 ml of fluid is then injected to load the pledget 18 from the adaptor 12 into the biopsy needle 16. Finally, about 0.3 ml of fluid is injected to deliver the pledget 18 into the biopsy tract. Loading of the pledget from the adaptor 12 into the needle 16 and delivery from the needle to the biopsy tract can be combined in one step by delivery of approximately 0.6 ml. Accurate and complete injection of the pledget with a minimum amount of extraneous fluid is achieved by this volumetric injection technique.

According to an alternative embodiment of the adaptor illustrated in FIG. 5, vent holes 44 extend through the side walls of the adaptor 12 adjacent the second end 34 for venting fluid during loading of the pledget 18. As illustrated in FIG. 5, the user places a finger over the second end 34 of the adaptor 12 to prevent the pledged from exiting the adaptor. The plunger 50 of the syringe 14 is then depressed, slowly causing fluid to pass into the adaptor 12 and hydrate the pledget. Preferably, the user waits a few seconds once the fluid is injected into the adaptor 12 until the pledget 18 is hydrated. Once the pledget 18 is hydrated, additional fluid is then injected quickly into the adaptor 12 to move the pledget 18 from the first end 30 of the adaptor toward the second end 34 of the adaptor. As the pledget 18 is compressed by the tapered section 42 of the adaptor 12 air and fluid are allowed to escape from the adaptor through the vent holes 44. Once the pledget 18 has been moved into the position illustrated in FIG. 5 adjacent the second end 34, fluid injection is halted. The adaptor 12 with the hydrated pledget 18 within the distal end is ready to insert the pledget through a biopsy needle to facilitate hemostasis within the biopsy tract.

As an alternative to placement of a finger at the distal end of the adaptor 12 during advancement of the pledget 18 through the tapered section 42, a removable vent cap may be used. Further, the vent holes 44 may be omitted and a screen or a cap having a screen may be used to allow fluid to pass through the screen while the screen prevents the pledget 18 from being ejected. One example of a vent cap will be described in further detail below with respect to FIGS. 14 and 15.

An alternative embodiment of the delivery system is illustrated in FIG. 7 in which an adaptor 12 is provided with a pressure indicator 64 to monitor pledget injection. Preferably, the pressure indicator 64 is removably attached at a luer fitting 66 provided on a side of the adaptor 12. The pressure indicator 64 includes a pressure dome 68 movable from the convex shaped extended position illustrated in FIG. 7 to a flat position depending on the pressure inside the adaptor 12. Internal pressure within the biopsy needle 16, the adaptor 12, and the syringe 14 will drop as the pledget 18 is extruded from the biopsy needle into the biopsy tract. This causes the pressure dome 68 to move from the convex position illustrated in FIG. 7 to a flat position, indicating that pledget delivery is complete.

Figure 8:
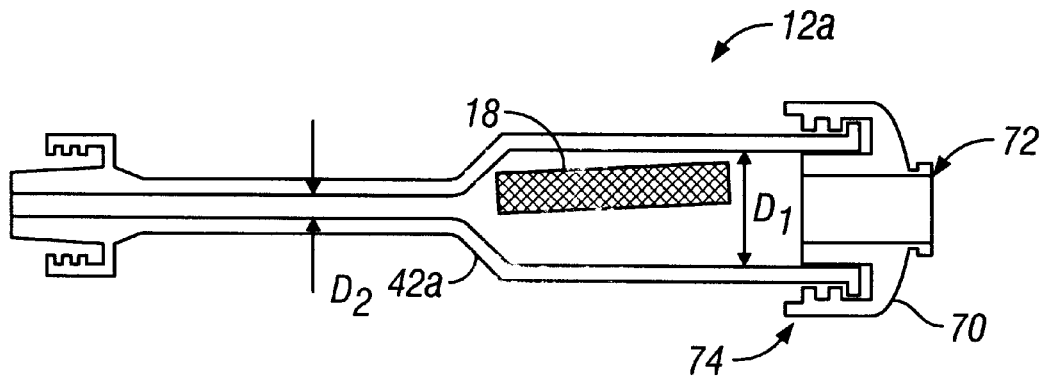
FIG. 8 is a side cross sectional view of an alternative embodiment of an adaptor.

FIG. 8 illustrates an alternative embodiment of an adaptor 12a in which the tapered section 42a is shorter and more abrupt. The particular size and shape of the adaptor 12a according to either FIG. 2 or FIG. 8 may vary depending on the size of biopsy needle, the tissue sample size, and the size of pledget to be delivered. One example of the adaptor 12a of FIG. 8 for delivery of an absorbable sponge pledget 18 through an approximately 18 gauge biopsy needle has a first adaptor diameter $D_1$ of about 0.25 cm or greater, preferably about 0.30 to 0.80 cm and a second adaptor diameter $D_2$ of about 0.25 cm or less, preferably, about 0.05 to 0.23 cm. An angle made by a wall of the tapered section 42a with a longitudinal axis of the adaptor 12a may vary from about 5° to 90°, but is preferably between about 30° and 60°. The tapered section 42a is illustrated with a substantially planar interior surface, when shown in cross section. However, the tapered section 42a may also have a convex or concave surface in cross section. The dimensions described for the adaptor 12a are appropriate for use with an approximately 18 gauge biopsy needle commonly used for liver biopsies. For some of the much larger biopsy needles or cannulas used for skin or breast biopsies the adaptor dimensions would be scaled up accordingly.

FIG. 8 also shows a connector 70 for connecting the adaptor 12 to a syringe 14 when the proximal end of the adaptor is larger in diameter than the standard syringe fitting. The connector 70 includes a first end 72 for connection to the syringe 14 and a second end 74 for connection to the adaptor 12.

One type of absorbable sponge material which is acceptable for use in the present invention is Gelfoam, manufactured by the Upjohn Company. Gelfoam is a porous, pliable, cross-linked gelatin material and is available commercially in sheet form as pre-compressed or non-compressed sponge. The material may be provided preformed as a pledget 18 or may be cut with a punch 10, or a stencil or template and knife to form a pledget as described above. Once hydrated, the pledget 18 can be easily compressed to fit into a lumen having a smaller cross sectional area than the original cross sectional area of the pledget. Additionally, the kneading of the hydrated pledget 18 during delivery encourages air trapped within the Gelfoam to be expelled and replaced with fluid, allowing rapid expansion upon delivery. When a pledget 18 of a pre-compressed Gelfoam is hydrated and kneaded (expelling air) during delivery, the pledget will have the absorption capacity to rapidly expand to many times (e.g., 3 or more times) its original dry volume upon delivery. When a pledget 18 of the non-compressed Gelfoam is hydrated and kneaded (expelling air) during delivery, the pledget will have the absorption capacity to rapidly expand to its original dry volume upon delivery. These properties make the Gelfoam sponge material particularly useful for facilitating hemostasis of biopsy sites.

Abrupt lumen diameter changes within or between the adaptor 12 or the needle 16 will cause "kneading" of the absorbable sponge material improving hydration of the absorbable sponge material thereby improving the expansion properties of the hydrated delivered absorbable sponge. According to the alternative embodiments of the adaptor illustrated in FIGS. 9 and 10, enlarged, recessed, or irregular areas in the lumen of the adaptor are provided to impart additional kneading action to the absorbable sponge material further improving the expansion properties of the sponge.

Figure 9:
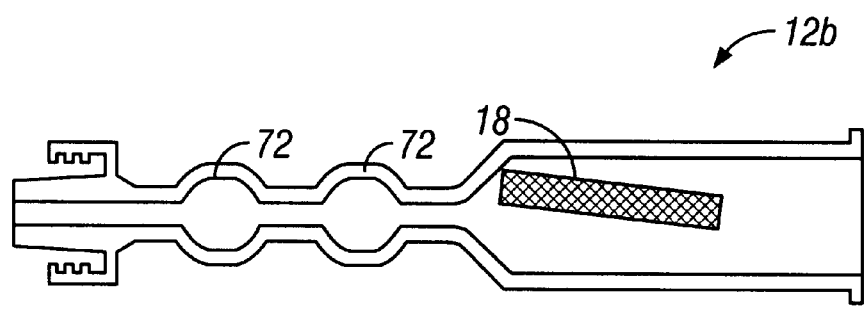
FIG. 9 is a side cross sectional view of an alternative embodiment of an adaptor with enlargements in the lumen for kneading the pledget.
Figure 10:
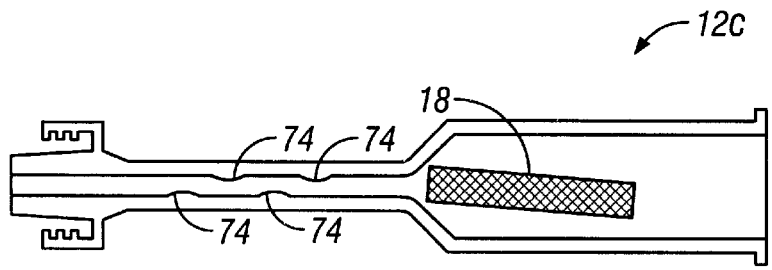
FIG. 10 is a side cross sectional view of an alternative embodiment of an adaptor with irregularities in the lumen for kneading the pledget.

The adaptor 12b of FIG. 9 includes two enlarged areas 72 of the lumen. As the absorbable sponge pledget 18 passes through the lumen of the adaptor 12b the material expands and is compressed by the adaptor to increase kneading of the pledget. FIG. 10 illustrates another alternative embodiment of the adaptor 12c including a lumen with a plurality of staggered irregularities 74 for improved kneading of the absorbable sponge pledget 18. The irregularities 74 will preferably have a relatively smooth surface to prevent the absorbable sponge material from becoming caught on the irregularities.

Figure 11:
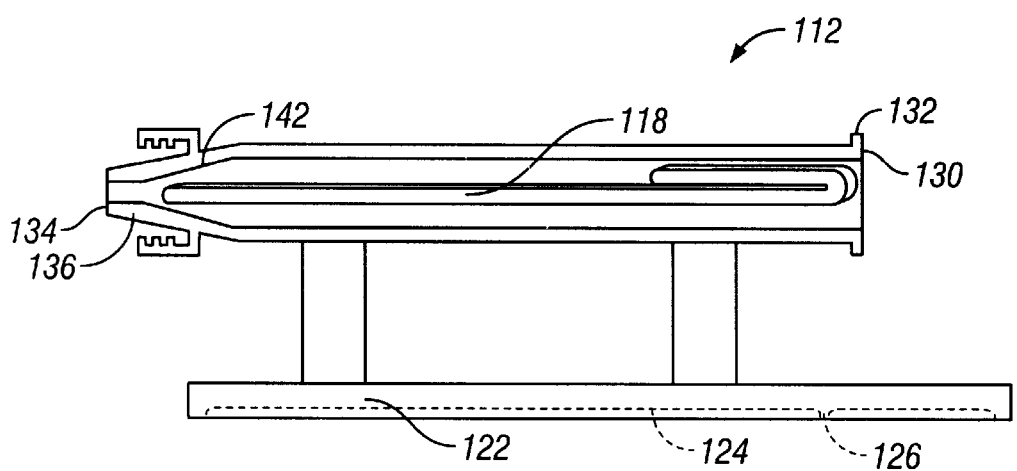
FIG. 11 is a side cross sectional view of an alternative embodiment of an adaptor for delivery of a pledget including a template attached to the adaptor.
Figure 12:
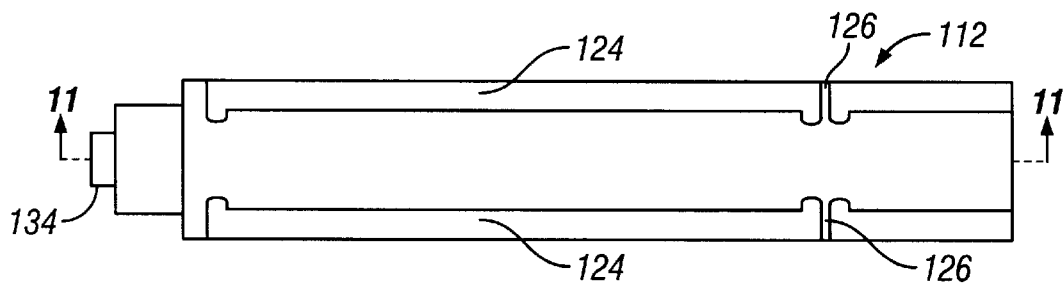
FIG. 12 is a bottom view of the adaptor and template of FIG. 11.

FIG. 11 illustrates an alternative embodiment of an adaptor 112 with a pledget formation template 122 attached to the adaptor. As shown in FIG. 11, the adaptor 112 includes a proximal end 130 having a female luer 132 and a distal end 134 having a male luer 136. The pledget 118 is inserted in the proximal end 130. A tapered section 142 is provided within the adaptor 112 for compressing the pledget 118 into the biopsy needle.

When delivering a pledget 118 of absorbable sponge material, it is important to deliver a desired amount of the sponge material using a minimum amount of fluid. Some devices and methods which allow the delivery of sponge material with a minimum amount of fluid include the use of the pledget configuration as illustrated in FIG. 11, the use of a vent cap for staging of the pledget as illustrated in FIGS.

Figure 16:
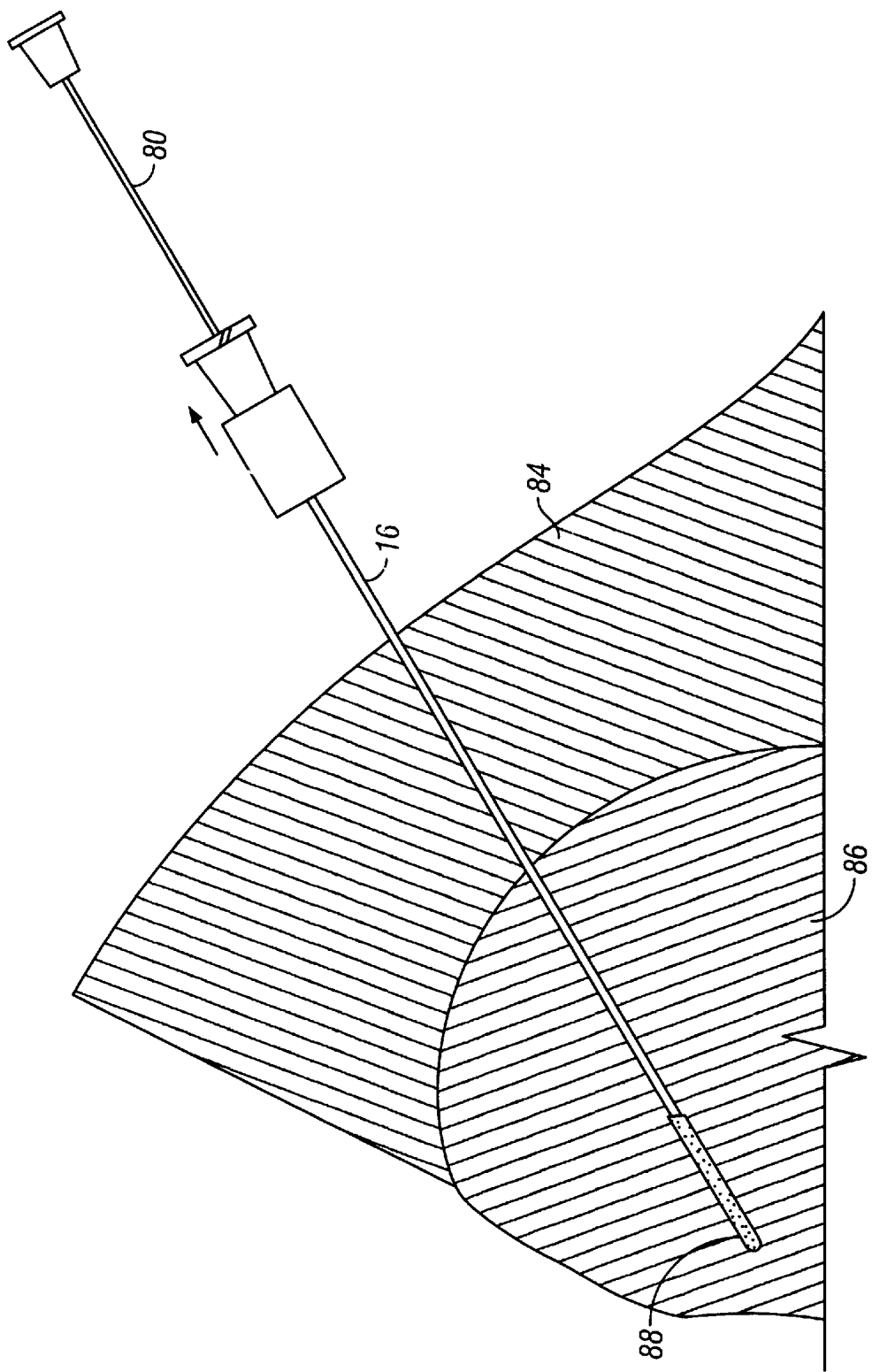
FIG. 16 is a side cross sectional view of a portion of an organ and a system for delivering a pledget into a biopsy tract in the organ.

14 and 15, and the withdrawal of the biopsy needle during delivery as illustrated in FIG. 16.

Pledgets 118 having increased proximal cross sectional areas are more easily delivered than pledgets with constant cross sectional areas or decreased proximal cross sectional areas. FIG. 11 illustrates a pledget 118 having a proximal cross sectional area which is approximately twice its distal cross sectional area. The smaller material mass at the distal end of the pledget 188 increases the ease of inserting the pledget into the adaptor 112. The smaller distal end of the pledget also passes through the delivery cannula or biopsy needle without creating a large back pressure to resist the delivery of the pledget through the cannula. The larger proximal section of the pledget 118 provides a better seal within the interior of the adaptor 112 and the cannula 16 which allows a minimum amount of fluid to be used to advance the pledget. The increased material at the proximal end of the pledget 118 also increases the amount of sponge material delivered to the biopsy tract.

Pledgets 118 with increased cross sectional area proximal ends may be prepared in a variety of manners. For example, if a pledget 118 is prepared from a sheet of sponge material, the increased proximal mass can be achieved by cutting the pledget with an enlarged proximal end. Alternatively, the pledget 118 may be formed by folding, rolling, compressing, or otherwise manipulating the sponge material to the desired shape. The proximal pledget mass may also be increased by adding separate pieces of material to the proximal end of the pledget. This additional material may be layered, wrapped, coiled or attached to the pledget in any other manner. The pledgets may also be formed by molding, bump extruding, dipping, or the like. The larger cross sectional area of the proximal end is generally about 1.2 to 4 times the cross sectional area of the distal end. In addition, the proximal end with the larger cross section area preferably extends along about ⅛ to ¾ of the total pledget length.

Figure 13:
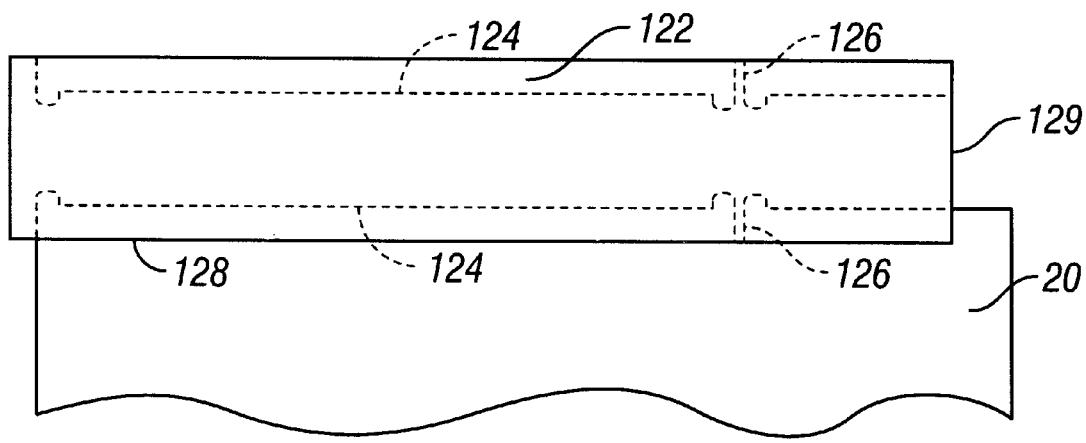
FIG. 13 is a top view of the template as it is used for cutting a pledget from an absorbable sponge sheet.

The pledget 118 illustrated in FIG. 11 has been formed by cutting a strip of material from an absorbable sponge sheet 20 with the aid of the template 122 as illustrated in FIG. 13. After the strip is cut, the proximal end of the strip is then folded back onto itself to form a pledget 118 with an increased cross sectional area and material mass at a proximal end. One example of a preferred embodiment of a Gelfoam pledget for delivery down a 20 gauge biopsy needle or cannula has a size of approximately 0.1×1.5×0.06 inches and is folded as illustrated in FIG. 11 to an overall length of about 0.9 inches. Placing this pledget 118 in an adaptor 112 having a largest internal diameter of 0.125 inches allows the pledget to be delivered to a 20 gauge or larger biopsy needle. Other common biopsy procedures use an 18 gauge or larger biopsy needle through a slightly larger guide cannula and would receive a somewhat larger pledget. After taking a core sample and removing the biopsy needle from the cannula guide, a pledget 118 maybe delivered through the cannula to the biopsy site. The pledget 118 for use in the system employing an 18 gauge or larger biopsy needle may be formed from a strip which is approximately 0.11–0.12 inches wide by about 3.125 inches long with a thickness of about 0.06 inches and folded to an overall length of about 2.2 inches. This pledget having a single thickness distal end and double thickness proximal end can be delivered from an adaptor having a largest internal diameter of approximately 0.125 inches.

One method for forming the pledget 118 with the enlarged proximal end with the aid of a template 122 is illustrated in FIG. 13. The template 122 is a flat plate having recesses 124 along one or more edges of the template. The recesses 124 have a width and a length which correspond to a preferred width and length of the pledget. The recesses 124 form a raised bar 126 at a location where the pledget should be folded. When the template is pressed onto a sheet 20 of absorbable sponge material, the bar 126 makes an indentation or groove in the sponge material. A user cuts along the side 128 and end 129 edges of the template 122 with a blade to form a strip of the sponge material which is then folded along the groove or crease formed by the bar 126 to form the pledget 118. It is important to securely hold the sponge sheet by applying downward pressure to the template 122 during cutting to prevent tearing and breaking of the sponge material. Prior to folding the strip of sponge material to form the pledget, the strip may be compressed with a flat surface of the template to compact the sponge and assist in loading the pledget into the adaptor 112.

Although the template 122 has been illustrated as a plate which is attached to the adaptor 112, it should be understood that the template can also be a separate member. In addition, the template 122 may provide guides for forming pledgets of different sizes for delivery through different sized biopsy needles. The template 122 may be provided with or without the creasing bar 126 and may be transparent or opaque. In the opaque version, the edges of the recess' 124 are used to align the template with an edge of the sponge sheet 20. In contrast, in a transparent version of the template, the recesses 124 may be eliminated and a visual indication or line may be provided which assists in aligning an edge of the sponge sheet with the template.

Figure 14:
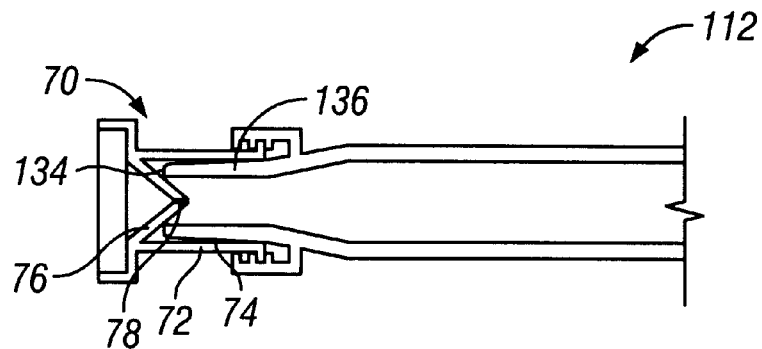
FIG. 14 is a side cross sectional view of a distal end of an adaptor with a vent cap attached.
Figure 15:
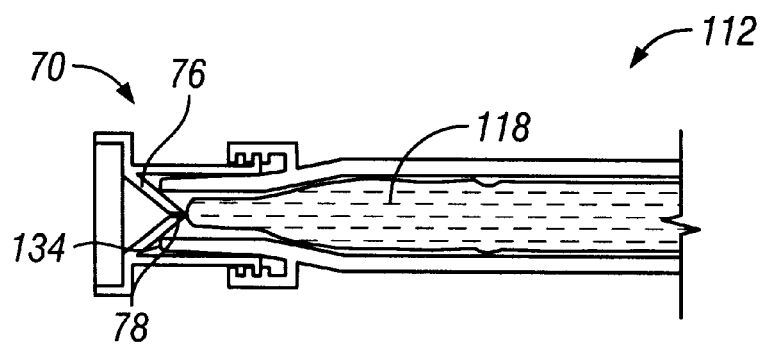
FIG. 15 is a side cross sectional view of the adaptor and vent cap of FIG. 14 having a pledget staged within the adaptor.

FIGS. 14 and 15 illustrate a preferred vent cap 70 for use with the adaptor 112. As discussed above with respect to FIG. 5, vents maybe used to assist in hydrating and staging the pledget within the adaptor. In particular, vents will allow the pledget to be moved to a preferred axial location within the adaptor 112 prior to delivery. In addition, the vents allow fluid to be injected and air to be removed from the pledget prior to delivery. The vent cap 70 as illustrated in FIG. 14 includes a female luer connector 72 including a flange 74 which is received on the male luer 136 of the adaptor 112. The vent cap 70 also includes a conical portion 76 which is configured to extend into a distal end 134 of the adaptor 112. The conical portion 76 has one or more fluid paths or vent holes 78 which allow air and fluid to exit through the vent cap but prevent the absorbable sponge material of the pledget 118 from passing through the vent cap. The vent hole may alternatively be positioned between the vent cap 70 and the adaptor 112. Preferably, an exterior of the conical portion 76 forms a seal with the lumen of the adaptor 112 at the distal end. The diameter of the vent hole 78 is approximately 0.005–0.02 inches, preferably approximately 0.01 inches. This small vent hole 78 allows the purging and venting of fluid and air from the adaptor 112 but does not allow the pledget 118 to pass through the vent hole, even at high pressures such as 5 mpsi or greater. The use of the vent cap 70 allows the user to apply high pressures with the syringe used to hydrate the pledget. The high pressures drive the fluid into the pledget causing rapid and thorough hydration of the sponge material. Repeated pulsing of the fluid with the syringe will provide more complete hydration of the pledget.

The vent cap 70 also positions the pledget 118 at a preferred axial position just proximal to the distal end 134 of the adaptor 112 as illustrated in FIG. 15. This positioning of the pledget 118 away from the end of the adaptor prevents the pledget from becoming trapped between the adaptor 112 and the biopsy needle hub 28 which is attached to the distal end of the adaptor. In addition, after hydration of the pledget and removal of the vent cap 70 the sponge material may tend to swell out of the distal end of the adaptor 112. Accordingly, the conical portion 76 of the vent cap 70 preferably extends into the adaptor 112 approximately 0.01 to 0.1 inches, more preferably about 0.01 to 0.03 inches.

The portion of the vent cap 70 which extends into the lumen of the adaptor 112 can be any desired shape such as dome-shaped, cylindrical, conical or other shape.

As described above, the pledget maybe delivered to the biopsy tract by holding the biopsy needle or cannula 16 stationary and injecting the pledget through the biopsy needle. If additional pledgets are to be delivered, the biopsy needle 16 is withdrawn a distance sufficient to accommodate an additional pledget and the additional pledget is then injected.

According to an alternative embodiment, the method of delivering the pledget into the biopsy tract may include withdrawing the biopsy needle or cannula 16 during delivery of the pledget 18 to deliver the pledget in an elongated trail which follows the biopsy tract. Placing the absorbable sponge material in a trail which fills the entire biopsy tract provides the added benefit of providing hemostasis along the entire biopsy tract. This is particularly helpful for stopping the bleeding of biopsy tracts in organs which tend to have excessive bleeding such as the liver, kidney, spleen, and other vascular organs.

In order to achieve a trail of absorbable sponge material in the biopsy tract, one method of the present invention involves the delivery of the pledget into the biopsy needle by a predetermined amount of fluid. The biopsy needle is then withdrawn at a velocity V while the pledget material is ejected from the biopsy needle at a velocity E with respect to the biopsy needle. The velocity V at which the biopsy needle is withdrawn is equal to or less than the velocity E at which the absorbable sponge material is delivered. The control of injection of fluid and withdrawal of the needle to achieve the desired trail of absorbable sponge material in the biopsy tract maybe controlled with an injection controlling device.

According to an alternative embodiment as illustrated in FIG. 16, the adaptor maybe used to deliver the pledget into the biopsy needle 16 and then the adaptor is removed from the biopsy needle. A plunger or stylet 80 which is generally provided with the biopsy needle 16 for inserting the biopsy needle is then used to deliver the pledget from the biopsy needle. As shown in FIG. 16, the biopsy needle extends through the tissue 84 and into the organ 86 for removal of a core of tissue. After a biopsy, the pledget is injected into the needle 16 and the plunger 80 is placed within the biopsy needle so that a distal end of the plunger abuts the proximal end of the pledget 118. The plunger 80 is then held stationary while the biopsy needle 16 is withdrawn from the biopsy site. The plunger 80 causes the pledget 118 to be delivered in a trail 88 which fills the biopsy tract. The trail 88 preferably extends along the entire biopsy tract to or past a surface of the organ 86. The delivery of the trail 88 of absorbable sponge material provides an advantage over the delivery of discrete blobs of material because the trail is able to provide hemostasis along the entire tract. In contrast, if a blob of absorbable sponge material is delivered within the tract at a depth of 1–2 cm from the surface of the organs, this 1–2 cm of biopsy tract may continue to bleed significantly.

As an alternative to delivery of the pledget as a trail, the pledget may be delivered as a plug. To deliver a plug the plunger 80 is advanced into the needle 16 pushing the pledget out of the distal end of the needle while the needle is held stationary. A combination of delivery of plugs and trails may also be used. The pledget material may be delivered entirely within a single anatomical structure or may cross two or more anatomical structures such as an organ, surrounding tissue and facial layer.

Although the invention is primarily intended for delivery of absorbable sponge, non-absorbable sponge may also be delivered with the devices, systems, and methods of the present invention. A non-absorbable sponge may be desirable where it will be necessary to locate the biopsy site or tract after the procedure.

Although the pledget 18 has been shown and described as having a rectangular cross section, pledgets of other shapes may also be used. For example, the pledget may be preformed in any shape, such as with a rectangular or circular cross section or may be rolled from a thin sheet of absorbable sponge material. The pledget 18 may have a multi-sided cross section, a star-shaped cross section, or a folded cross section and may have through or blind holes formed in the dry pledget. In addition, the pledget size and shape can be matched to the size and shape of a particular delivery site. Pledget shapes having greater surface area provided by features such as fins provide faster hydration.

Figure 17:
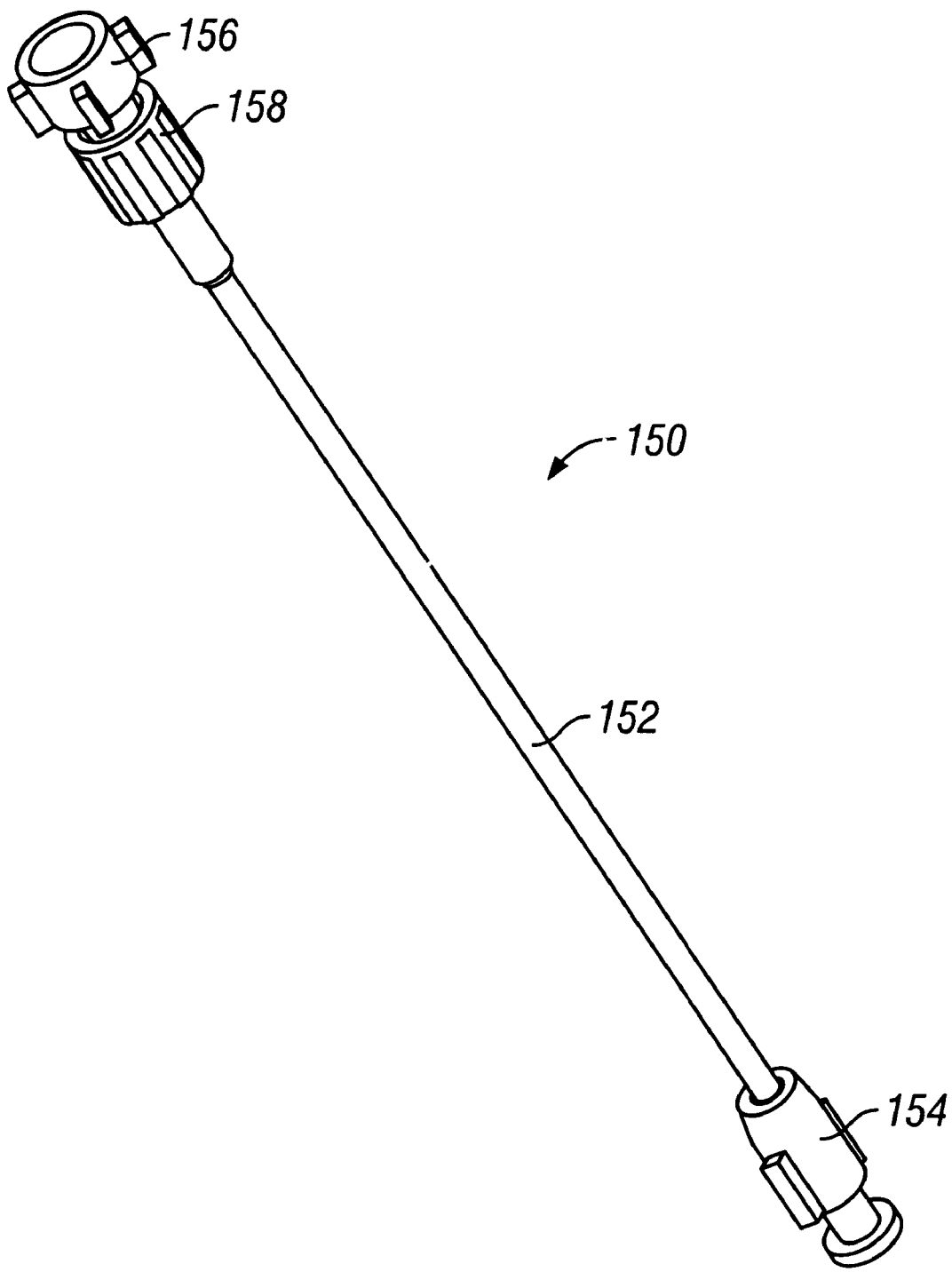
FIG. 17 is a perspective view of a trail staging device for use with the present invention.

The continuous structure of the absorbable sponge pledget 18 provides more secure and reliable placement than a paste or liquid and can even facilitate partial withdrawal, removal, or movement of the delivered pledget. However, in some cases the pledget may sheer, tear, or otherwise break apart when it is delivered through some small needles leaving the delivered pledget in pieces in the biopsy tract. The trail staging chamber 150 as shown in FIG. 17 allows the user to visualize the elongated pledget prior to delivery of the pledget into the biopsy needle or other cannula.

The trail staging chamber 150 includes an elongated transparent tube 152 having a proximal fitting 154 for connection to the adaptor 12 and a distal fitting 158 for connection to the biopsy needle 16 or cannula. A vent cap 156 may also be provided which is connectable to the distal fitting 158. A vent cap 156 increases the ability to maintain the continuity of the pledget during the delivery of the pledget from the adaptor 12 to the trail staging chamber 150.

In use, the pledget is delivered from the adaptor 12 into the trail staging chamber 150 by injection of fluid until a distal end of the pledget contacts the vent cap 156. The elongated pledget is visualized within the staging chamber 150 to determine whether continuity of the pledget has been maintained. If gaps or spaces are viewed, the pledget is discarded by removing the vent cap 156 and expelling the pledget. A new pledget is then injected into the staging chamber 150. Once a continuous pledget has been observed in the staging chamber 150, the staging vent cap 156 is removed, the staging chamber is connected to the biopsy cannula, and the pledget is delivered to the biopsy tract as described above. The vent cap 156 may have a variety of configurations such as those described above for use with the adaptor. Alternatively, a vent hole may be used in place of the vent cap.

Pledget discontinuities are often the result of uncontrolled advancement of the pledget, which causes a portion of the pledget to tear away or separate from the pledget proximal to it. The vent cap 156 helps to maintain the continuity of the pledget during delivery of the pledget from the adaptor 12 to the trail staging chamber 150. In one embodiment, the vent cap 156 is provided with a vent of sufficient size to create back pressure or resistance as the pledget is delivered from the adaptor to the trail staging chamber 150. As the pledget is delivered to the trail staging chamber 150, the pledget displaces media which is in front of it. The displaced media escapes through the vent. The resistance provided by the vent acts as a damper to beneficially limit or control an undesirable, sudden advancement of a portion of the pledget from the adaptor 12 to the trail staging chamber 150. Therefore, discontinuities of the pledget are minimized or eliminated.

It will also be apparent to one skilled in the art that by using a non-compressible fluid or viscous fluid as the media that it will provide additional dampening benefits to the pledget as it is delivered from the adaptor 12 to the trail staging chamber 150.

As shown in FIGS. 18–24, alternative embodiments of the vent cap are disclosed. The vent caps include a valve member which has an opened and a closed position. In the closed position, the valve members are designed to provide a back pressure or resistance in the trail staging chamber 150 to the pledget as it is delivered from the adaptor 12. When a certain force is applied against a valve member, the valve member moves from the closed position to the opened position, wherein a gas and/or a fluid may pass through the vent cap.

Figure 18:
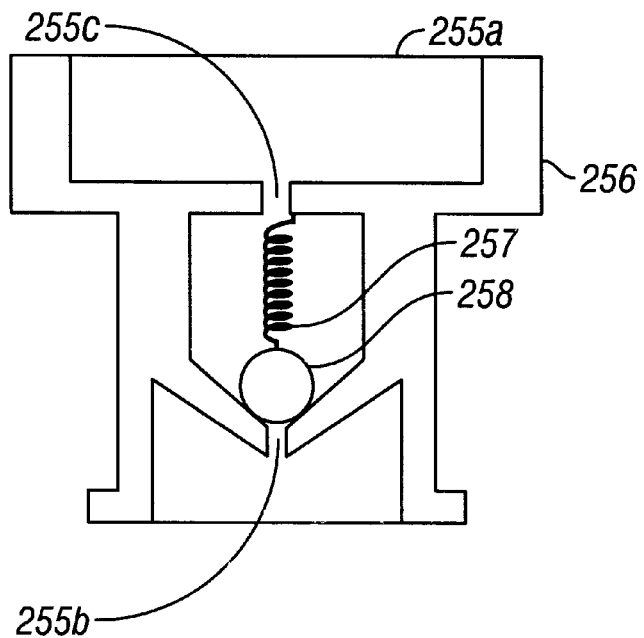
FIG. 18 is a side cross sectional view of an alternative embodiment of a vent cap.

For example, in FIG. 18, an alternative embodiment of the vent cap is shown wherein the vent cap 256 has a vent hole 255 and a spring 257 which biases a ball valve 258. The vent hole 255 extends through the vent cap 256 and includes a sequence of openings. The sequence of openings include a proximal opening 255*a*, a distal opening 255*b*, and an intermediate opening 255*c* which is located between the proximal and distal openings. As shown, the ball valve 258 is in a closed position, whereby the spring 257 biases the ball valve to occlude the distal opening 255*b*.

In operation, a hydrated pledget 118 is advanced from the adaptor 12 to the trail staging chamber 150 so that the pledget displaces the gas and/or fluid (i.e., media) which is in front of the pledget. This displacement of media purges the trail staging chamber 150. When the media exerts sufficient force against the ball valve 258, the ball valve moves from the closed position to an opened position so that the media can pass through the distal opening 255*b*. Accordingly, the spring biased ball valve 258 acts as a one-way valve which allows a gas or a fluid to pass through the vent hole 255.

Figure 19:
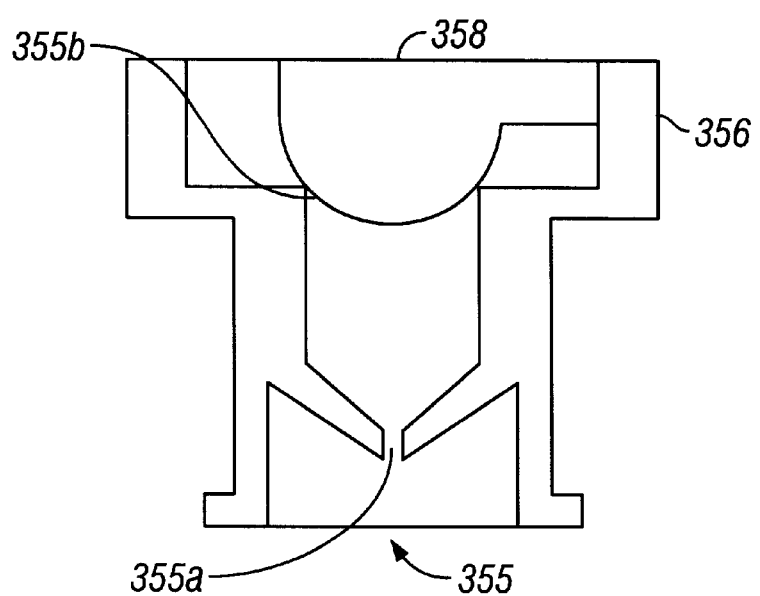
FIG. 19 is a side cross sectional view of an alternative embodiment of a vent cap.

In another embodiment of the vent cap, as shown in FIG. 19, the vent cap 356 includes a vent hole 355 and a flapper valve 358 which is in a closed position. The vent hole 355 extends through the vent cap 356 and includes a proximal opening 355*a* and a distal opening 355*b*. As in the embodiment of FIG. 18, when the pledget displaces the media, the media will exert a force against the flapper valve 358. When the media exerts sufficient force against the flapper valve 358, the flapper valve moves from the closed position to an opened position so that the media can pass through the distal opening 355*b*. Accordingly, the flapper valve 358 acts as a one-way valve which allows a gas or a fluid to pass through the vent hole 355.

Figure 20:
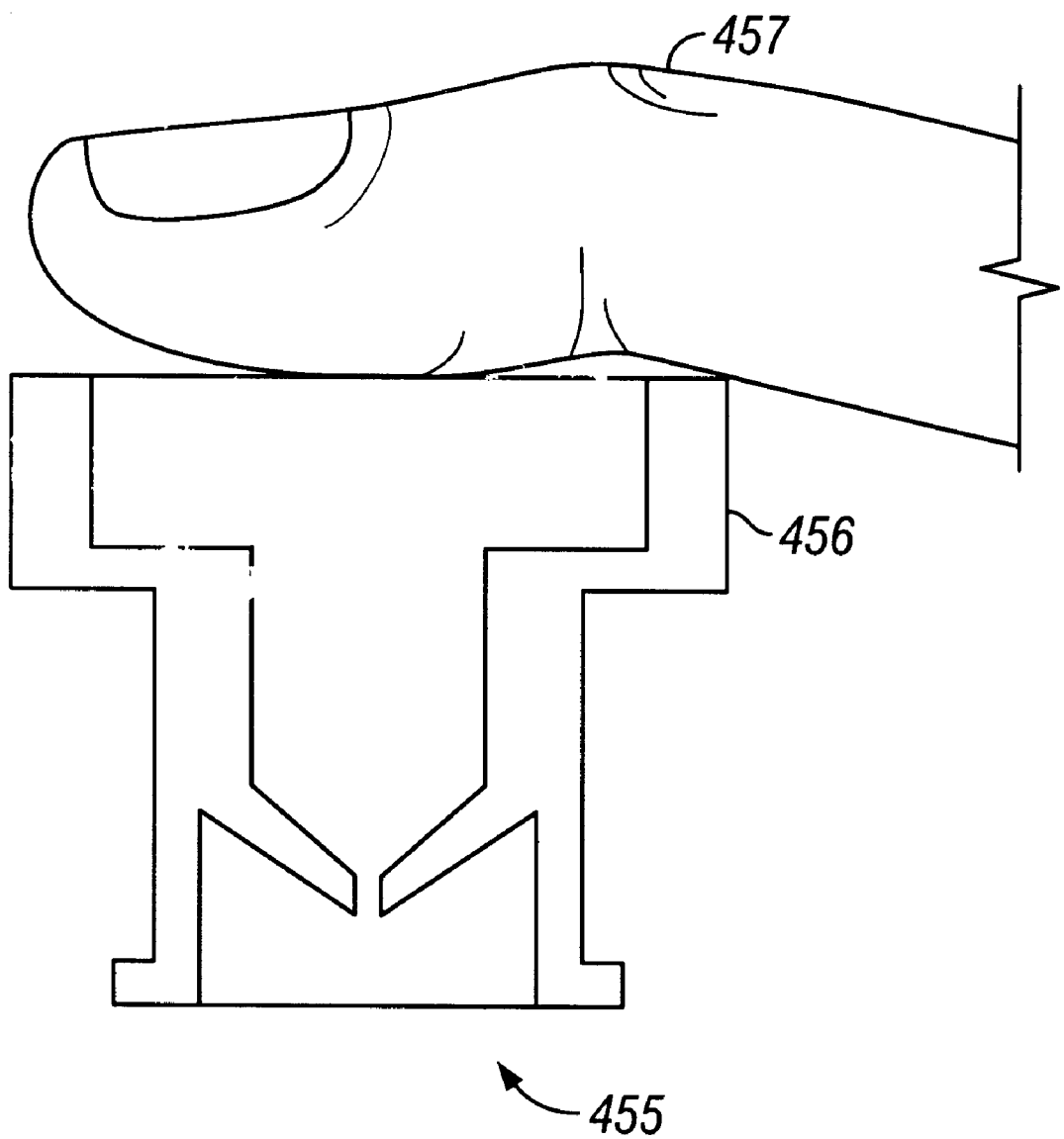
FIG. 20 is a side cross sectional view of an alternative embodiment of a vent cap.

As shown in FIG. 20, in yet another embodiment of the vent cap, the vent cap 456 is substantially similar to the embodiment of FIG. 19, except that a finger 457 can be used to act as a valve member. When the finger 457 is closed over the vent hole 455, the finger provides a back pressure or resistance in the trail staging chamber 150 to the pledget as it is delivered from the adaptor 12.

Figure 21:
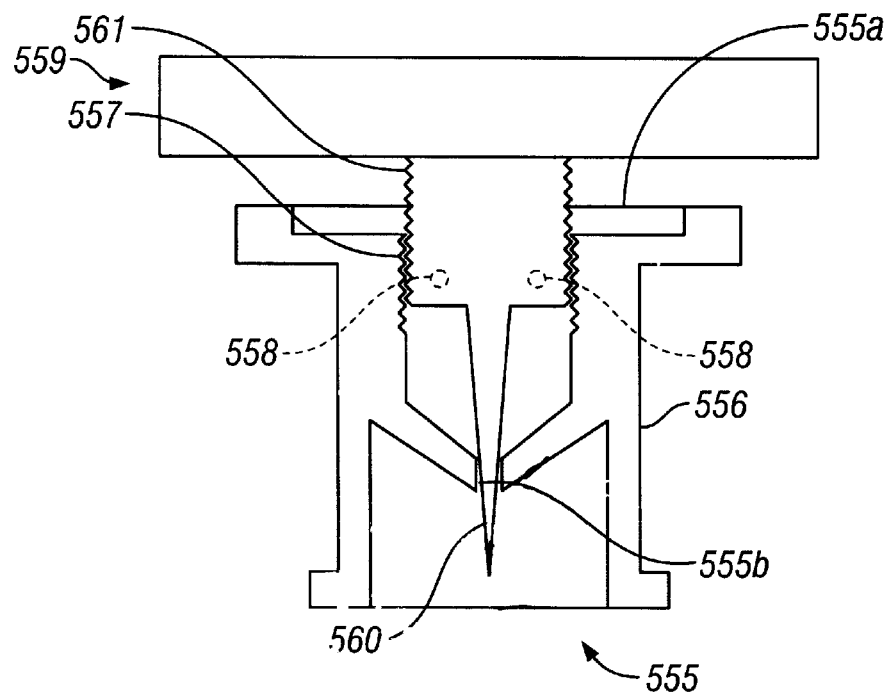
FIG. 21 is a side cross sectional view of an alternative embodiment of a vent cap in a closed position.
Figure 22:
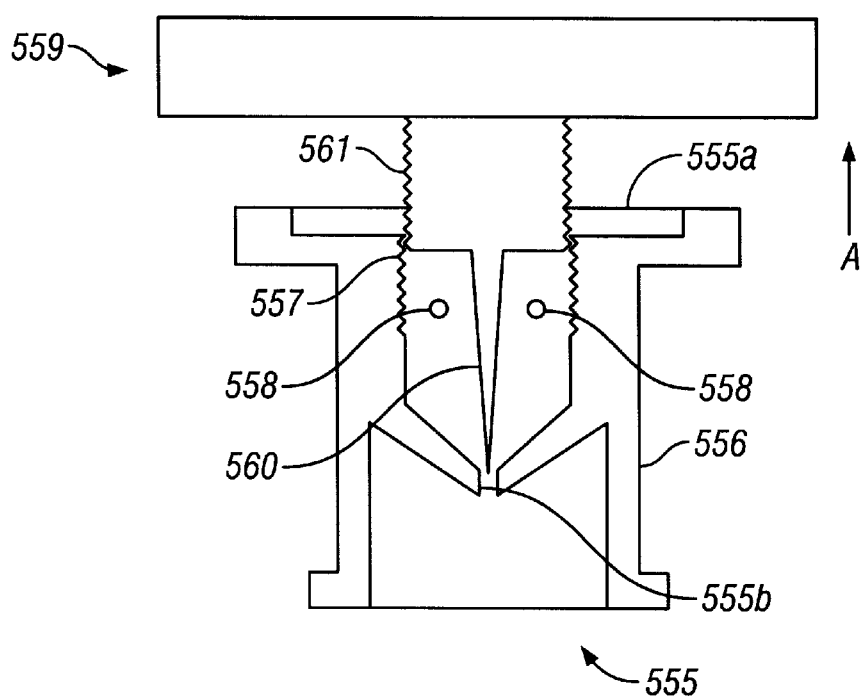
FIG. 22 is a side cross sectional view of the vent cap shown FIG. 21 in an opened position.

FIGS. 21 and 22 illustrate an alternative embodiment of the vent cap 556 which includes a vent hole 555, a threaded portion 557, and at least one drain hole 558. A needle valve 559 has a needle extending member 560 and a threaded portion 561 which engages the threaded portion 557 of the vent cap 556. The vent hole 555 includes a proximal opening 555*a* and a distal opening 555*b*. As shown in FIG. 21, when the needle valve 559 is in a closed position, the needle extending member 560 extends through the distal opening 555*b*, thereby occluding that opening and blocking the drain holes 558. By rotating the needle valve 559, the user may change the position of the needle valve. In particular, the needle valve can be moved in the direction of arrow A from the closed position of FIG. 21 to the opened position, as shown in FIG. 22. In the opened position, the needle extending member 560 does not occlude the distal opening 555*b*, so that a gas and/or a fluid can pass through the distal opening and through the drain holes 558 to exit the vent cap 556.

Figure 23:
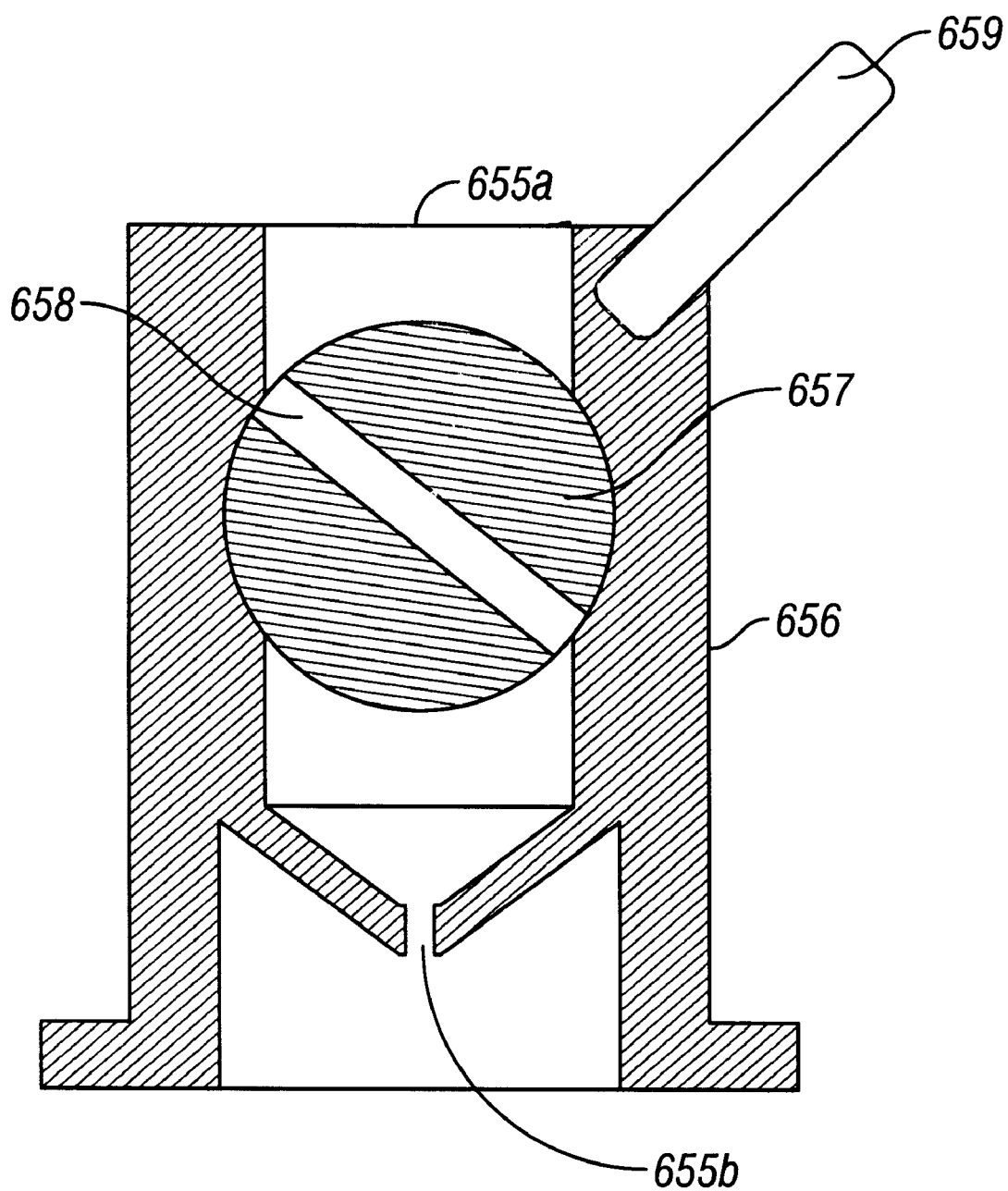
FIG. 23 is a side cross sectional view of an alternative embodiment of a vent cap in a closed position.
Figure 24:
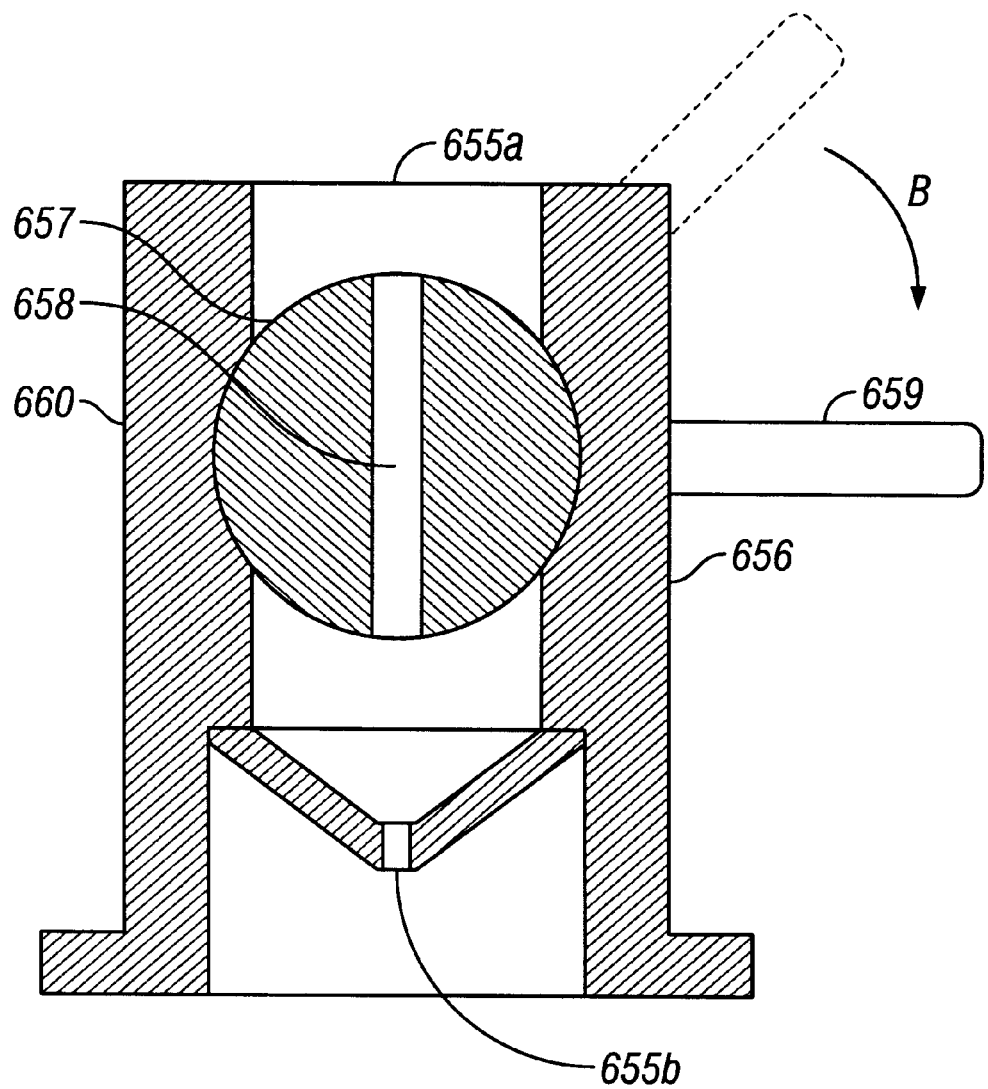
FIG. 24 is a side cross sectional view of the vent cap shown in FIG. 23 in an opened position.

In yet a further embodiment of the vent cap, as shown in FIGS. 23 and 24, the vent cap 656 includes a vent hole 655 which extends through the vent cap. The vent hole 655 includes a proximal opening 655*a* and a distal opening 655*b*. A stop cock valve 657 has a passage 658 and is connected to a handle 659. The stop cock valve 657 is rotatably mounted in the vent cap 656 at a position located between the proximal and distal openings 655*a*, 655*b*. As shown in FIG. 23, the stop cock valve 657 is in a closed position, wherein the stop cock valve is positioned so that the passage 658 is obstructed. As shown in FIG. 24, the stop cock valve 657 is slidable along the surface of the vent hole 655, and the handle 659 can pivotally rotate the stop cock valve in a direction of arrow B from the closed position of FIG. 23 to an opened position. When the stop cock valve 657 is in the opened position, a gas and/or a fluid can pass through the distal opening 655*b* and through the passage 658 to exit the vent cap 656. Further, the stop cock valve 657 forms a seal with the vent cap 656, thereby preventing leakage of gasses or fluids from the adaptor 12 while the stop cock valve is in the closed position.

Many types of manual, self-actuated, or adjustable valves are readily apparent to one skilled in the art. The valve member may alternatively comprise any suitable means including, but not limited to, a Touhy-borst valve or other means for controlling or regulating the flow of a gas or fluid from the adaptor 12 to the trail staging chamber 150. It is readily appreciated that any of these embodiments can interface with or be incorporated into the distal end of the trail staging chamber.

Figure 25:
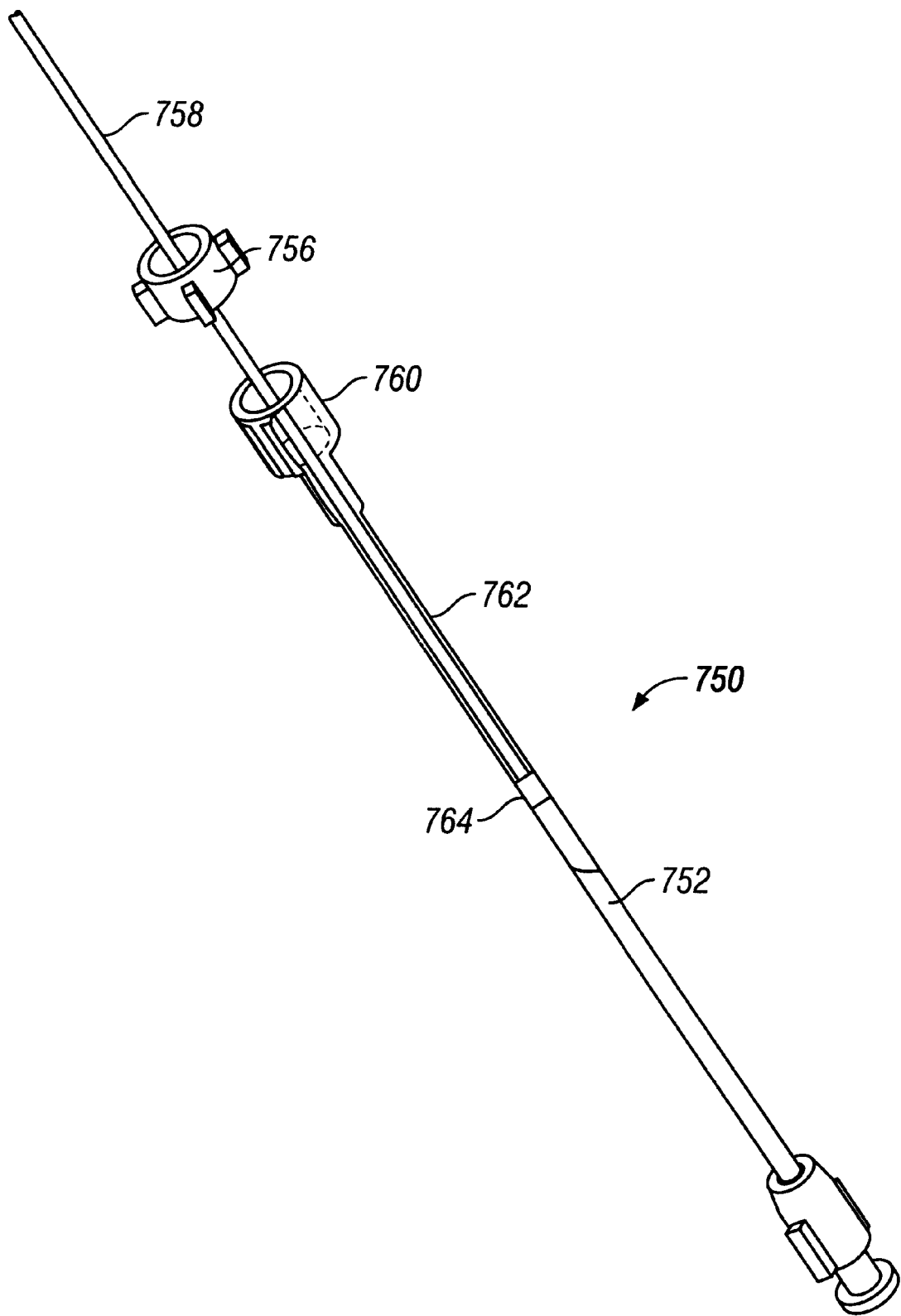
FIG. 25 is an exploded partial cross-sectional perspective view of the trail staging device with a rod extending into the trail staging device for use with the present invention.

In an alternative embodiment, as shown in FIGS. 25 and 26, a mechanical interface 758, such as a rod, may act as a damper to beneficially limit or control an undesirable sudden advancement of a portion of the pledget. The rod 758 extends through a vent hole 755 of a vent cap 756 and is slidably movable with respect to the vent cap 756. Further, the rod 758 is designed such that it fits in sliding relation with the elongated transparent tube 752 of the trail staging chamber 750. The vent cap 756 can couple with the distal end 760 of the trail staging chamber 750. The rod 758 extends to occupy at least a portion, and preferably an entire length, of the lumen 762 of the elongated transparent tube 752. The rod 758 may further include a stopping member 764 to position the pledget to a desired distal location within the trail staging chamber 750. It is understood that the stopping member 764 fits in sliding relation with the lumen 762 of the elongated transparent tube 752. The stopping member 764 may have a roughened surface to facilitate gripping between the stopping member and the lumen 762 of the elongated transparent tube 752. The roughened surface enhances the friction between the surfaces and may comprise any suitable means including, but not limited to, grooves, ridges, or ribs.

In an alternative embodiment, the rod 758' has an interference fit with the vent cap 756' such that a predetermined axial force is required from the media to move the rod with respect to the vent cap. The interference fit could be adjustable by providing an adjustable compression ring on the vent cap 756' or an adjustable set screw within the cap.

In another embodiment, the stopping means 764" is provided with an interference fit with the lumen 762" of the elongated transparent tube 752". In this configuration, a predetermined axial force, such as a force applied from the media, is required to move the stopping means 764" and the rod 758" with respect to the elongated transparent tube 752". In this embodiment, it is possible to omit the vent cap 756".

In still another embodiment shown in FIG. 27, an external axial force is applied to the rod 858 such as by a spring 860. The spring 860 couples the vent cap 856 to one end of the rod 858. Or in another alternative embodiment, a dashpot mechanism may be used in place of the spring 860.

It should be understood by those skilled in the art that any means of applying external force to the rod will provide the resistance or dampening to the pledged as it is delivered from the adaptor 12 to the trail staging chamber 150. For example, the operator's fingers providing external force to the rod, if applied properly, can create the desired back pressure or resistance sought in the above disclosed embodiment.

The ability to deliver a continuous trail of the pledget material to a biopsy tract is particularly important in some types of biopsies and is less important in others. For example, when performing a biopsy of the lung a pneumothorax or hemothorax may occur when the delivery of the pledget material is discontinuous. A pneumothorax occurs when air or gas accumulates in the pleural space and a hemothorax occurs when blood accumulates in the pleural space.

The internal diameter of the transparent tube 152 is smaller than the largest internal diameter $D_1$ of the adaptor and is preferably between the smallest internal diameter $D_2$ of the adaptor and the internal diameter of the needle or cannula. The length of the transparent tube 150 may vary depending on the length of the trail of pledget material which is to be delivered.

While the preferred embodiment of the trial staging chamber 150 is transparent or translucent, it should be appreciated that when the internal diameter of the staging chamber is between $D_2$ of the adaptor and the internal diameter of the needle, the odds of a continuous trail are improved by use of the trail staging chamber 150 with or without the added benefit of visualization. Thus, an opaque trial staging chamber 150 may also be used.

In some instances it may be desirable to deliver multiple pledgets in spaced apart positions along the biopsy tract, particularly for a long biopsy tract. For delivery of additional pledgets, the biopsy needle 16 is retracted a distance sufficient to provide a space to accommodate an additional pledget 18 and the injection procedure described above is repeated for the additional pledget(s). For a particularly large biopsy site or cavity, additional pledgets 18 may be injected beside an initially injected pledget until the cavity is filled.

Although a biopsy is most commonly performed by biopsy needle, a biopsy may also be performed through other cannulas, such as catheters, long needles, endoscopes, or the like. The treatment procedure according to the present invention can be used for facilitating hemostasis of puncture wounds through different types of cannulas including needles, catheters, endoscopes, and the like. In addition, the treatment procedure and systems according to the present invention may be used to deliver absorbable or non-absorbable sponge for other therapies, such as embolization. For example, sponge may be delivered for cosmetic or reconstructive bulking or for temporary or permanent intravascular embolization.

The absorbable sponge pledget 18 may be used to deliver a beneficial agent, such as contrast agent, thrombin, radiation treatment, or the like. The pledget can also be used to deliver therapeutic agents, such as radioactive isotopes for localized treatment of tumors, anti-cancer agents, anti-metastatic agents, and the like. Examples of anti-cancer agents include 5-fluorouracil, cisplatin, prednisone, and others described in U.S. Patent No. 4,619,913 which is incorporated herein by reference. The absorbable sponge pledget 18 may be presoaked with the beneficial agent for delivery to the biopsy tract. Alternatively, the pledget 18 may be hydrated with the beneficial liquid agent or the agent may be delivered to the pledget after the pledget is placed within the biopsy tract.

A pledget formed of commercially available Gelfoam material will be absorbed by the body within 1 to 6 weeks. However, the pledget material may be designed to provide different rates of absorption. For example, Gelfoam can be designed to be absorbed at different rates by varying the degree of cross-linking. Preferably, the pledget is designed to be absorbed in less than one month.

The treatment of a biopsy tract with a hydrated and injected pledget 18 of absorbable sponge to facilitate hemostasis provides substantial advantages in comfort over external pressure methods. In addition, the present invention also provides advantages over the insertion of an absorbable sponge material in a dry state with an applicator. In particular, the adaptor 12 allows a relatively large pledget to be compressed and inserted into the biopsy tract in a hydrated state. The injected pledget 18 conforms in shape quickly to the shape of the biopsy tract and immediately begins blocking blood flow. In contrast, a dry piece of sponge material must be cut to the particular size of the biopsy tract and does not swell to fill the tract until the blood has sufficiently saturated the sponge material which can take significantly longer and provides inadequate local compression.

While the invention has been described in detail with reference to the preferred embodiments thereof, it will be apparent to one skilled in the art that various changes and modifications can be made and equivalents employed, without departing from the present invention.

What is claimed is:

1. A device for improving delivery of hemostatic material, the device comprising:
   a vent cap body capable of removably engaging a cannula, the vent cap body having a passage extending through the vent cap body from the cannula when engaged to the vent cap to an exterior of the vent cap body, and a restricter for restricting a fluid from flowing from the cannula when engaged to the vent cap to the exterior through the passage.

2. The device for improving delivery of hemostatic material according to claim 1, wherein the restricter for restricting the fluid from flowing from the cannula to the exterior includes a valve.

3. The device for improving delivery of hemostatic material according to claim 2, wherein the valve is a spring biased ball valve.

4. The device for improving delivery of hemostatic material according to claim 2, wherein the valve is a flapper valve.

5. The device for improving delivery of hemostatic material according to claim 2, wherein the valve is a needle valve.

6. The device for improving delivery of hemostatic material according to claim 2, wherein the valve is a stop cock valve.

7. The device for improving delivery of hemostatic material according to claim 1, wherein the device includes a rod which extends through the passage of the vent cap body from the cannula to an exterior of the vent cap body.

8. A device for improving delivery of hemostatic material, the device comprising:
- a vent cap body capable of removably engaging a cannula, the vent cap body having a passage extending through the vent cap body from the cannula when engaged to the vent cap to an exterior of the vent cap body, a restricter for restricting a fluid from flowing from the cannula when engaged to the vent cap to the exterior through the passage; and
- a rod which extends through the passage of the vent cap body from the cannula to an exterior of the vent cap body, wherein the rod is slidably movable with respect to the vent cap and cannula.

9. The device for improving delivery of hemostatic material according to claim 8, wherein the rod includes a stopping member.

10. The device for improving delivery of hemostatic material according to claim 9, wherein the stopping member is provided with an interference fit with the cannula.

11. The device for improving delivery of hemostatic material according to claim 7, wherein the rod has an interference fit with the vent cap, such that a predetermined axial force is required to move the rod with respect to the vent cap.

12. The device for improving delivery of hemostatic material according to claim 7, wherein an external force is applied to the rod by a spring.

13. A device for improving delivery of hemostatic material, the device comprising:
- a vent cap body capable of removably engaging a cannula, the vent cap body having a passage extending through the vent cap body from the cannula when engaged to the vent cap to an exterior of the vent cap body, a restricter for restricting a fluid from flowing from the cannula when engaged to the vent cap to the exterior through the passage, wherein the restricter for restricting the fluid from flowing from the cannula to the exterior includes an opening sized to sealably engage a finger.

14. A system for improving delivery of hemostatic material, the system comprising:
- an elongated cannula having a first end, a second end, and a lumen extending from the first end to the second end; and
- a vent cap body capable of removably engaging the second end, the vent cap body having a passage extending through the vent cap body from the cannula to an exterior of the vent cap body, and a restricter for restricting a fluid from flowing from the cannula to the exterior through the passage.

15. The system for improving delivery of hemostatic material according to claim 14, wherein the restricter for restricting the fluid from flowing from the cannula to the exterior includes a valve.

16. The system for improving delivery of hemostatic material according to claim 15, wherein the valve is a spring biased ball valve.

17. The system for improving delivery of hemostatic material according to claim 15, wherein the valve is a flapper valve.

18. The system for improving delivery of hemostatic material according to claim 15, wherein the valve is a needle valve.

19. The system for improving delivery of hemostatic material according to claim 15, wherein the valve is a stop cock valve.

20. The system for improving delivery of hemostatic material according to claim 14, wherein the restricter for restricting the fluid from flowing from the cannula to the exterior includes an opening sized to sealably engage a finger.

21. The system for improving delivery of hemostatic material according to claim 14, further comprising an extending member sized to fit within the removable vent cap.

22. The system for improving delivery of hemostatic material according to claim 21, wherein the extending member is slidably mounted within the vent cap.

23. The system for improving delivery of hemostatic material according to claim 22, wherein the extending member forms an interference fit within the lumen of the elongated cannula.

24. The system for improving delivery of hemostatic material according to claim 14, wherein the system includes a rod which extends through the passage of the vent cap body from the cannula to an exterior of the vent cap body.

25. The system for improving delivery of hemostatic material according to claim 24, wherein the rod is slidably movable with respect to the vent cap and cannula.

26. The system for improving delivery of hemostatic material according to claim 24, wherein the rod includes a stopping member.

27. The system for improving delivery of hemostatic material according to claim 24, wherein the rod has an interference fit with the vent cap, such that a predetermined axial force is required to move the rod with respect to the vent cap.

28. The system for improving delivery of hemostatic material according to claim 26, wherein the stopping member is provided with an interference fit with the cannula.

29. The system for improving delivery of hemostatic material according to claim 24, wherein an external force is applied to the rod by a spring.

30. A method of preparing and delivering hemostatic material to a patient, the method comprising:
- inserting a pledget of sponge material into a cannula;
- connecting a vent cap to the cannula;
- restricting a flow of fluid through the cannula and vent cap by use of a restricter;
- hydrating the sponge; and
- delivering the hydrated sponge to the patient.

31. The method of preparing and delivering hemostatic material to a patient according to claim 30, wherein the sponge material is positioned axially within the cannula by the vent cap.

32. The method of preparing and delivering hemostatic material to a patient according to claim 30, wherein the vent cap is removed before delivery of the pledget.

33. The method of preparing and delivering hemostatic material to a patient according to claim 30, wherein the vent cap has a valve.

34. The method of preparing and delivering hemostatic material to a patient according to claim 33, wherein the valve is a spring biased ball valve.

35. The method of preparing and delivering hemostatic material to a patient according to claim 33, wherein the valve is a flapper valve.

36. The method of preparing and delivering hemostatic material to a patient according to claim 33, wherein the valve is a needle valve.

37. The method of preparing and delivering hemostatic material to a patient according to claim 33, wherein the valve is a stop cock valve.

38. The method of preparing and delivering hemostatic material to a patient according to claim 30, wherein the restricter for restricting the fluid from flowing through the cannula and vent cap to the exterior includes an opening sized to sealably engage a finger.

39. The method of preparing and delivering hemostatic material to a patient according to claim 30, further comprising positioning a rod which extends through the passage of the vent cap body from the cannula to an exterior of the vent cap body.

40. The method of preparing and delivering hemostatic material to a patient according to claim 39, wherein the rod is slidably movable with respect to the vent cap and cannula.

41. The method of preparing and delivering hemostatic material to a patient according to claim 39, wherein the rod includes a stopping member.

42. The method of preparing and delivering hemostatic material to a patient according to claim 39, wherein the rod has an interference fit with the vent cap, such that a predetermined axial force is required to move the rod with respect to the vent cap.

43. The method of preparing and delivering hemostatic material to a patient according to claim 41, wherein the stopping member is provided with an interference fit with the cannula.

44. The method of preparing and delivering hemostatic material to a patient according to claim 39, wherein an external force is applied to the rod by a spring.

* * * * *